(12) United States Patent  
Mitchell et al.

(10) Patent No.: US 7,964,597 B2
(45) Date of Patent: Jun. 21, 2011

(54) PIPERAZINYL-SULFONAMIDE DERIVATIVES USEFUL IN THE TREATMENT OF GPR38 RECEPTOR MEDIATED DISEASES

(75) Inventors: Darren Jason Mitchell, Stevenage (GB); Jonathan Thomas Seal, Stevenage (GB); Geoffrey Stemp, Stevenage (GB); Mervyn Thompson, Harlow (GB); Susan Marie Westaway, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/744,367

(22) PCT Filed: Nov. 26, 2008

(86) PCT No.: PCT/EP2008/066213
§ 371 (c)(1),
(2), (4) Date: May 24, 2010

(87) PCT Pub. No.: WO2009/068552
PCT Pub. Date: Jun. 4, 2009

(65) Prior Publication Data
US 2010/0256364 A1 Oct. 7, 2010

(30) Foreign Application Priority Data
Nov. 28, 2007 (GB) .................................. 0723317.4

(51) Int. Cl.
*A61K 31/5377* (2006.01)
*A61K 31/496* (2006.01)
*C07D 295/12* (2006.01)
*C07D 401/12* (2006.01)
*C07D 401/14* (2006.01)
*C07D 413/14* (2006.01)

(52) U.S. Cl. ............ 514/235.8; 514/252.12; 514/253.12; 544/121; 544/360; 544/364; 544/398

(58) Field of Classification Search .................... None
See application file for complete search history.

(56) References Cited

FOREIGN PATENT DOCUMENTS
WO   WO 2007/012479 A   2/2007
WO   WO 2008/000729 A   1/2008

*Primary Examiner* — Emily Bernhardt
(74) *Attorney, Agent, or Firm* — Kathryn L. Sieburth; John Lemanowicz

(57) ABSTRACT

Disclosed are motilin agonists, processes for their preparation, pharmaceutical compositions containing them and their use in the treatment of various disorders.

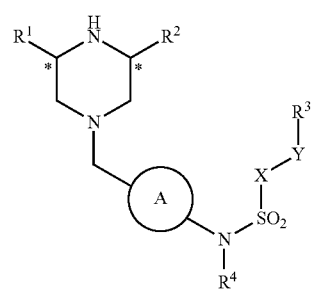

9 Claims, No Drawings

PIPERAZINYL-SULFONAMIDE DERIVATIVES USEFUL IN THE TREATMENT OF GPR38 RECEPTOR MEDIATED DISEASES

This application is a 371 of International Application No. PCT/EP2008/066213, filed 26 Nov. 2008, which claims the priority of GB 0723317.4, filed 28 Nov. 2007, which are incorporated herein in their entireties.

The present invention relates to novel compounds having pharmacological activity, processes for their preparation, pharmaceutical compositions containing them and their use in the treatment of various disorders.

GPR38 is a 7-transmembrane, G-protein coupled receptor, with high affinity for the peptide motilin [Feighner et al., Science 1999, 284, 2184], suggesting that endogenous motilin exerts all or most of its activity via this receptor.

Motilin is a 22 amino acid peptide found in large amounts within endocrine-like cells of the gastrointestinal tract, and especially in the duodenum-jejunum areas. During fasting, the peptide is known to be associated with the onset of Phase III migrating complex activity within the stomach [Boivin et al., Dig. Dis. Sci. 1992, 37, 1562], suggesting a role in the mechanisms of prokinetic activity. Motilin is also released from the gut during feeding, sham feeding, gastric distension or by oral or intravenous nutrient application [Christofides et al., Gut 1979, 20, 102; Bormans et al., Scand. J. Gastroenterol. 1987, 22, 781], suggesting additional roles for this peptide in the modulation of motility patterns during feeding.

In animals or in man, motilin has long been known to increase gastrointestinal motility, and promote gastric emptying and intestinal propulsion in an anal direction, during both fasting and fed conditions. This activity is thought to be primarily due to a facilitation of at least the cholinergic excitatory function of the gut [Van Assche et al., Eur. J. Pharmacol. 1997, 337, 267], perhaps also involving the activation of the vagus nerve [Mathis & Malbert, Am. J. Physiol. 1998, 274, G80]. In addition, higher concentrations of motilin directly evoke a small contraction of the muscle [Van Assche et al., Eur. J. Pharmacol. 1997, 337, 267].

The antibiotic erythromycin was shown to mimic the gastrointestinal activity of motilin, in addition to its previously-described antibiotic properties [see Peeters, in *Problems of the Gastrointestinal Tract in Anaesthesia* Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., Analyt. Biochem. 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disorders (GERD). Finally, erythromycin has been used to promote intestinal propulsive activity, finding clinical utility in the treatment of pseudo-obstruction and in conditions with impaired colonic motility [Peeters, in *Problems of the Gastrointestinal Tract in Anaesthesia* Ed., Herbert M K et al. Springer-Verlag, Berlin, Heidelberg 1999, pp 39-51].

Consequently it is expected that agonists at the GPR38 receptor will mimic the activity of motilin and find clinical utility in the treatment of gastrointestinal disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs. Interestingly, the ability of motilin or erythromycin to activate the vagus nerve, the association of this nerve with changes in feeding behaviour [e.g. Furness et al., Auton. Neurosci. 2001, 92, 28] and the chromosomal location of GPR38 [based on Ensembl: 13q21.1 (58.46-59.46 Mb)] within the markers (D135257-13q14.11 to D135258 at 13q21.33) of a locus associated with obesity [Feitosa et al, Am. J. Hum. Genet. 2002, 70, 72] also suggests that agonists active at the GPR38 receptor will, in addition to promoting gastrointestinal motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote gastrointestinal motility, the association of motilin gene polymorphism with Crohn's disease [Annese et al., *Dig. Dis. Sci.* 1998, 43, 715-710] and the changes in motilin receptor density during colitis [Depoortere et al., *Neurogastroenterol. Motil.* 2001, 13, 55] suggests a utility for agonists at the motilin receptor for the treatment of inflammatory bowel conditions in general.

Finally, GPR38 is also found in regions outside the gastrointestinal tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the gastrointestinal and feeding utilities already mentioned, but in addition, suggests an involvement of the receptor in a greater spectrum of vagal-hypothalamic functions.

WO9410185, EP838469, WO9823629, DE19805822, and U.S. Pat. No. 6,165,985 claim erythromycin derivatives targeting GPR38 for use in disorders relating to gastrointestinal motility. WO9921846, WO0185694, WO0168620, WO0168621, and WO0168622 disclose a series of small molecule antagonists of the GPR38 receptor. JP07138284 and EP807639 disclose peptide agonists. JP09249620, WO02092592, WO05027637, US2005065156 and Li et al., (2004, Journal of Medicinal Chemistry, 47(7) p 1704-1708) disclose series of small molecule agonists.

A structurally novel class of compounds has now been found which provides partial or full agonists of the GPR38 receptor.

The present invention therefore provides compounds of formula (I) or pharmaceutically acceptable salts thereof:

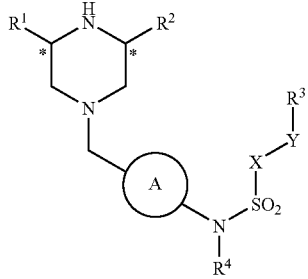
(I)

wherein
A is a phenyl or a 6-membered heteroaryl ring, each optionally substituted with up to three substituents independently selected from halogen, $C_{(1-4)}$alkyl, $CF_3$ and $C_{(1-4)}$alkoxy;
$R^1$ and $R^2$ are independently H or $C_{(1-4)}$ alkyl;
$R^3$ is a phenyl, 5 or 6 membered heteroaryl ring, or 5 or 6 membered heterocyclyl ring, each optionally substituted;
X is a phenyl, 5 or 6 membered heteroaryl ring, or 5 or 6 membered heterocyclyl ring each optionally substituted and each connected to the sulfonamide sulfur atom via a carbon atom; and
Y is a bond, $NR^5$, O or $CH_2$;
$R^4$ is hydrogen or $C_{(1-4)}$ alkyl.
$R^5$ is hydrogen or $C_{(1-4)}$ alkyl.

The present invention therefore provides compounds of formula (IA) or pharmaceutically acceptable salts or solvates thereof:

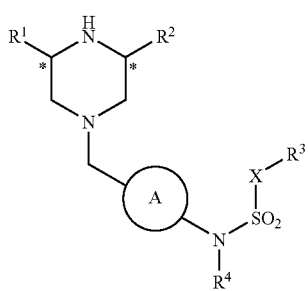
(IA)

wherein
A is a phenyl or a 6-membered heteroaryl ring, each optionally substituted with up to three substituents independently selected from halogen, $C_{(1-4)}$alkyl, $CF_3$ and $C_{(1-4)}$alkoxy;
$R^1$ and $R^2$ are independently H or $C_{(1-4)}$ alkyl;
$R^3$ is a phenyl, heteroaryl, or heterocyclyl ring each optionally substituted;
X is a phenyl, heteroaryl, or heterocyclyl ring each optionally substituted and each connected to the sulfonamide sulfur atom via a carbon atom; and
$R^4$ is hydrogen or $C_{(1-4)}$ alkyl.

When $R^3$ or X is substituted, it may have 1, 2 or 3 substituents, each independently selected from halogen, $C_{(1-4)}$alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^5$, $NR^5R^6$, $NHCOR^5$, $NHSO_2R^5$, $C(O)CF_3$, $C(O)C_{(1-4)}$alkyl, $C(O)C_{(3-7)}$cycloalkyl, $C(O)OC_{(1-4)}$alkyl, $C(O)OC_{((3-7)}$cycloalkyl, $OC(O)C_{(1-4)}$alkyl, $OC(O)C_{(3-7)}$cycloalkyl, $CONH_2$, $CONHR^5$, $CONR^5R^6$, $SOR^6$, $SO_2CF_3$, $SO_2R^6$, $OSO_2R^6$, $OSO_2CF_3$, $SO_2NH_2$, $SO_2NHR^5$, $SO_2NR^5R^6$, where $R^5$ and $R^6$ may be the same or different and represent $C_{(1-4)}$ alkyl, phenyl optionally substituted with halogen or 5 or 6 membered heteroaryl optionally substituted with halogen.

The term "alkyl" as a group or part of a group e.g. alkoxy or hydroxyalkyl refers to a straight or branched alkyl group in all isomeric forms. The term "$C_{(1-4)}$alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, or tert-butyl, Examples of such alkoxy groups include methoxy, ethoxy, propoxy, iso-propoxy, butoxy, iso-butoxy, sec-butoxy and tert-butoxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents a 5 or 6 membered unsaturated ring which comprises one or more heteroatoms. When the term heteroaryl represents a 5 membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

The term "heterocyclyl ring" represents a saturated or partially saturated 5 or 6 membered ring which comprises one or more heteroatoms selected from nitrogen, oxygen and sulphur. Examples of such heterocyclyl groups include pyrrolidinyl, piperidinyl, piperazinyl and morpholinyl.

One embodiment of the invention are compounds of formula (I) wherein:
A is phenyl optionally substituted with up to three substituents independently selected from halogen, $C_{(1-4)}$alkyl, $CF_3$ and $C_{(1-4)}$alkoxy; and/or
$R^1$ is hydrogen or methyl; and/or
$R^2$ is hydrogen or methyl; and/or
$R^3$ is optionally substituted phenyl, morpholinyl or piperidinyl; and/or
X is optionally substituted phenyl or pyridyl; and/or
$R^4$ is hydrogen or methyl; and/or
Y is a bond, NH, $NCH_3$ or $CH_2$.

In one embodiment A is phenyl optionally substituted by $C_{(1-4)}$alkyl or $CF_3$. In another embodiment A is unsubstituted phenyl. In a further embodiment A is phenyl substituted with methyl or $CF_3$.

In one embodiment $R^1$ is hydrogen. In another embodiment $R^1$ is methyl.

In one embodiment $R^2$ is hydrogen. In another embodiment $R^2$ is methyl

In one embodiment $R^3$ is optionally substituted phenyl. In another embodiment $R^3$ is phenyl optionally substituted by halo. In another embodiment $R^3$ is phenyl optionally substituted by fluoro.

In another embodiment $R^3$ is optionally substituted morpholinyl. In a further embodiment $R^3$ is unsubstituted morpholinyl. In another embodiment $R^3$ is optionally substituted piperidinyl. In a further embodiment $R^3$ is unsubstituted piperidinyl.

In one embodiment X is optionally substituted phenyl. In a further embodiment X is unsubstituted phenyl.

In one embodiment X is optionally substituted pyridyl. In a further embodiment X is unsubstituted pyridyl.

In one embodiment R⁴ is hydrogen. In another embodiment R⁴ is methyl.

In one embodiment Y is a bond.
In another embodiment Y is NH.
In a further embodiment Y is NCH₃.
In another embodiment Y is CH₂.

One embodiment of the invention are compounds of formula (IA) wherein:
A is optionally substituted phenyl; and/or
R¹ is hydrogen or methyl; and/or
R² is hydrogen or methyl; and/or
R³ is optionally substituted phenyl, morpholinyl or piperidinyl; and/or
X is optionally substituted phenyl or pyridyl; and/or
R⁴ is hydrogen or methyl.

It is to be understood that the present invention covers all combinations of substituent groups described hereinabove.

In a further embodiment of the invention the (piperazinyl)methylene group and [—N(R⁴)—SO₂—X—Y—R³] group are para- to each other across ring A and, where X represents optionally substituted phenyl or pyridyl, the [(piperazinyl)methylene-A-N(R⁴)—SO₂—] group and [—Y—R³] group are either para- or meta- to each other across ring X.

In certain of the compounds of formula (I), dependent upon the nature of the substituent there are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses. Preferred compounds of formula (I) wherein R¹ and R² are both methyl are those wherein the piperazine C* carbons have the 3R,5S-configuration. Preferred compounds of formula (I) wherein one of R¹ and R² is methyl and the other is hydrogen are those wherein the piperazine C* carbon has the S-configuration.

Certain of the compounds herein can exist in various tautomeric forms and it is to be understood that the invention encompasses all such tautomeric forms.

Suitable compounds of the invention are:
6-(4-Fluorophenyl)-N-methyl-N-(4-{[(3S)-3-methyl-1-piperazinyl]methyl}phenyl)-3-pyridinesulfonamide
6-(4-Fluorophenyl)-N-(4-{[(3S)-3-methyl-1-piperazinyl]methyl}phenyl)-3-pyridinesulfonamide
N-(4-{[(3S)-3-Methyl-1-piperazinyl]methyl}phenyl)-6-(1-piperidinyl)-3-pyridinesulfonamide
N-(4-{[(3S)-3-Methyl-1-piperazinyl]methyl}phenyl)-6-(4-morpholinyl)-3-pyridinesulfonamide
4'-Fluoro-N-methyl-N-(4-{[(3S)-3-methyl-1-piperazinyl]methyl}phenyl)-4-biphenylsulfonamide
4'-Fluoro-N-(4-{[(3S)-3-methyl-1-piperazinyl]methyl}phenyl)-4-biphenylsulfonamide
N-(4-{[(3R,5S)-3,5-Dimethyl-1-piperazinyl]methyl}phenyl)-6-(4-fluorophenyl)-3-pyridinesulfonamide
6-(4-Fluorophenyl)-N-(3-methyl-4-{[(3S)-3-methyl-1-piperazinyl]methyl}phenyl)-3-pyridinesulfonamide
6-[(4-Fluorophenyl)amino]-N-methyl-N-(3-methyl-4-{[(3S)-3-methyl-1-piperazinyl]methyl}phenyl)-3-pyridinesulfonamide
5-(4-Fluorophenyl)-N-(3-methyl-4-{[(3S)-3-methyl-1-piperazinyl]methyl}phenyl)-3-pyridinesulfonamide
6-[(4-Fluorophenyl)methyl]-N-(4-{[(3S)-3-methyl-1-piperazinyl]methyl}phenyl)-3-pyridinesulfonamide
6-(4-Fluorophenyl)-N-[4-{[(3S)-3-methyl-1-piperazinyl]methyl}-3-(trifluoromethyl)phenyl]-3-pyridinesulfonamide
6-[(4-Fluorophenyl)amino]-N-(4-{[(3S)-3-methyl-1-piperazinyl]methyl}phenyl)-3-pyridinesulfonamide
6-[(3-Fluorophenyl)amino]-N-(4-{[(3S)-3-methyl-1-piperazinyl]methyl}phenyl)-3-pyridinesulfonamide
6-[(4-Fluorophenyl)(methyl)amino]-N-(4-{[(3S)-3-methyl-1-piperazinyl]methyl}phenyl)-3-pyridinesulfonamide The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In a further aspect, this invention provides a process for the preparation of a compound of formula (I)

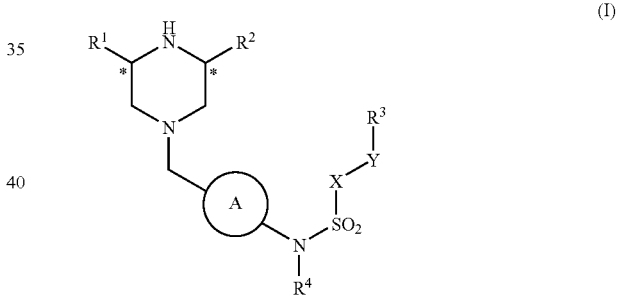

as defined above or a pharmaceutically acceptable salt or solvate thereof, which process comprises reacting a compound of formula (II)

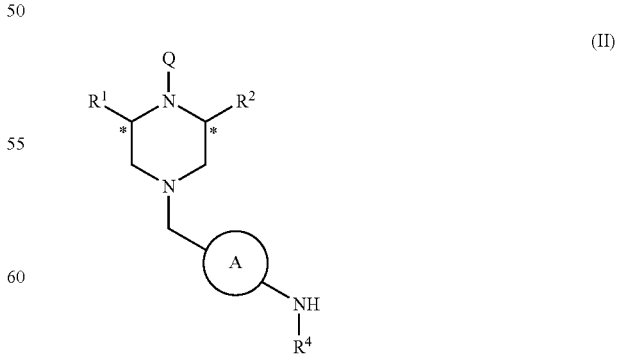

wherein R¹, R², A and R⁴ are as defined above and Q is hydrogen or a suitable nitrogen protecting group such as tert-butyloxycarbonyl (Boc) or benzyloxycarbonyl (Cbz), with a compound of formula R³—Y—X—SO₂-L¹ (formula (III)) wherein R³, X and Y are as defined above and L¹ is a leaving group such as halogen using conditions suitable for the formation of an sulfonamide bond. For example, where L¹ represents halogen, the reaction may be carried out using a suitable base such as triethylamine in an inert solvent such as dichloromethane.

And thereafter optionally carrying out one or more of the following reactions:

1. Converting one compound of formula (I) into another compound of formula (I);
2. Removing any protecting group;
3. Forming a suitable pharmaceutically acceptable salt or solvate of the compound so formed.

It will be appreciated by those skilled in the art that it may be necessary to protect certain reactive substituents during some of the above procedures. Standard protection and deprotection techniques, such as those described in Greene T. W. & Wuts P. G. M., Protective groups in organic synthesis, 2$^{nd}$ Edition, New York, Wiley (1991), can be used. For example, primary and secondary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluoroacetic acid in a suitable solvent such as dichloromethane, diethyl ether, 1,4-dioxane, isopropanol or mixtures thereof.

Compounds of formula R³—Y—X—SO₂-L¹ (III) are commercially available or may be prepared according to methods described in the literature or may be prepared by analogous or similar methods.

Compounds of formula (II) where A represents a 1,4-phenylene group and R⁴ represents $C_{(1-4)}$ alkyl may be prepared by reaction of a compound of formula (IV)

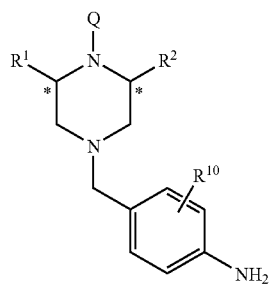

(IV)

wherein R¹ and R² are as defined above, R¹⁰ represents optional substitution in the phenylene moiety as defined for A above and Q is hydrogen or a suitable nitrogen protecting group such as tert-butyloxycarbonyl (Boc) or benzyloxycarbonyl (Cbz) with an appropriate aldehyde or ketone to provide R⁴, using conditions suitable for a reductive amination; for example in the presence of a suitable reducing agent such as sodium borohydride and in a suitable solvent such as methanol.

Compounds of formula (IV) may be prepared by reaction of a compound of formula (V)

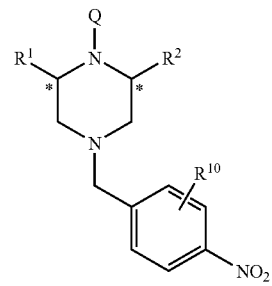

(V)

wherein R¹, R², R¹⁰ and Q are as defined above, using conditions suitable for a reduction; for example when Q is Boc, hydrogenation in the presence of a suitable catalyst such as palladium on charcoal or platinum on charcoal, in a suitable solvent such as methanol and optionally in the presence of a suitable base such as potassium hydroxide or triethylamine. Alternatively when Q is Boc or Cbz, the reduction may be carried out using a suitable metal reducing agent such as iron powder, in the presence of a suitable proton source such as ammonium chloride and in a suitable solvent such as aqueous methanol.

Compounds of formula (V) may be prepared by reaction of a compound of formula (VI)

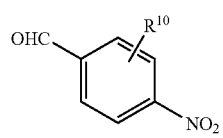

(VI)

wherein R¹⁰ is as defined above, with a compound of formula (VII),

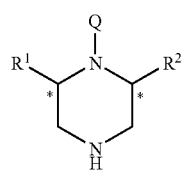

(VII)

wherein R¹, R² and Q are as defined above, using reaction conditions suitable for a reductive amination, for example in the presence of a reducing agent such as sodium tri(acetoxy) borohydride in a suitable solvent such as dichloromethane or 1,2-dichloroethane.

Alternatively compounds of formula (V) may be prepared by reaction of a compound of formula (VIII)

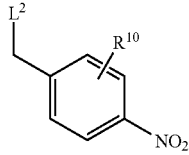
(VIII)

wherein $R^{10}$ is as defined above and $L^2$ represents a leaving group such as halogen, alkylsulfonyloxy or arylsulfonyloxy, with a compound of formula (VII) as defined above, using conditions suitable for an alkylation reaction, for example use of an appropriate solvent such as N,N-dimethylformamide and a suitable base such as Hunig's base.

An alternative process for preparation of compounds of formula (IV) comprises reaction of a compound of formula (VII) as defined above with a compound of formula (IX):

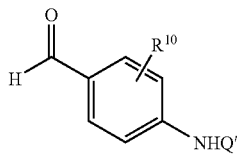
(IX)

wherein A and $R^{10}$ are as defined above and Q' is a suitable protecting group such as acetyl under conditions suitable for reductive amination as described above, followed by a deprotection step.

An alternative process for preparation of compounds of formula (I) wherein Y is a bond comprises reaction of a compound of formula (X)

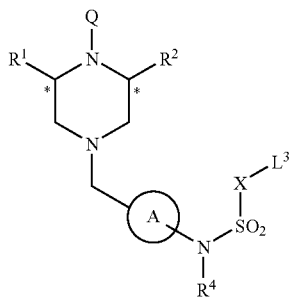
(X)

wherein $R^1$, $R^2$, $R^4$, A, X and Q are as defined above and $L^3$ represents a leaving group such as halogen with a compound of formula H—$R^3$ (formula (XI)) wherein $R^3$ is an optionally substituted 5 or 6 membered heterocyclyl group optionally in the presence of a suitable base such as potassium carbonate, caesium carbonate or Hunig's base and optionally using a suitable transition metal catalyst system such as palladium acetate/BINAP or copper (I) chloride/2,2,6,6-tetramethyl-3,5-heptanedione, and thereafter optionally carrying out modifications according to reactions 1-3 as described above.

An alternative process for preparation of compounds of formula (I) wherein X is optionally substituted phenyl or heteroaryl and Y is a bond comprises reaction of a compound of formula (X)

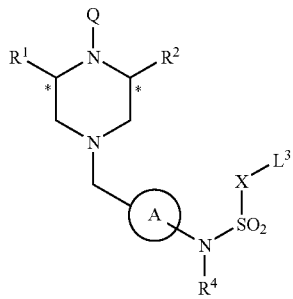
(X)

wherein $R^1$, $R^2$, $R^4$, A, X and Q are as defined above and $L^3$ represents a leaving group such as halogen with a compound of formula $R^3$—B(OH)$_2$ (formula (XII)) wherein $R^3$ is optionally substituted phenyl or heteroaryl, using a Suzuki reaction using a suitable transition metal catalyst system such as palladium (II) acetate/triphenylphosphine, tetrakis(triphenylphosphine)palladium or bis(triphenylphosphinepalladium (II) chloride, in the presence of a suitable base such as potassium carbonate or sodium carbonate and in a suitable solvent such as 1,2-dimethoxyethane and thereafter optionally carrying out modifications according to reactions 1-3 as described above.

Compounds of formula $R^3$—B(OH)$_2$ (formula XII)) are commercially available or may be prepared using methods similar to those described in J. P. Corbet and G. Mignani, Chem. Rev, 2006, 106, 2651 and F. Bellina et al., Synthesis, 2004, 15, 2419.

An alternative process for preparation of compounds of formula (I) wherein X is optionally substituted phenyl or heteroaryl and Y is NR$^5$ comprises reaction of a compound of formula (X)

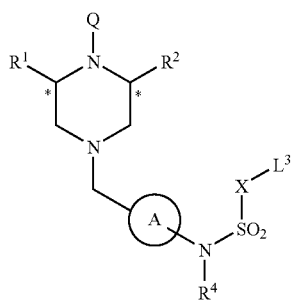
(X)

wherein $R^1$, $R^2$, $R^4$, A, X and Q are as defined above and $L^3$ represents a leaving group such as halogen with a compound of formula $R^3R^5$NH (formula XIII) wherein $R^3$ is optionally substituted phenyl or heteroaryl and $R^5$ is as defined above, in the presence of a suitable transition metal catalyst system such as palladium (II) acetate/BINAP, in the presence of a suitable base such as cesium carbonate and in a suitable solvent such as 1,4-dioxane and thereafter optionally carrying out modifications according to reactions 1-3 as described above.

An alternative process for preparation of compounds of formula (I) wherein X is optionally substituted phenyl or heteroaryl and Y is CH$_2$ comprises reaction of a compound of formula (X)

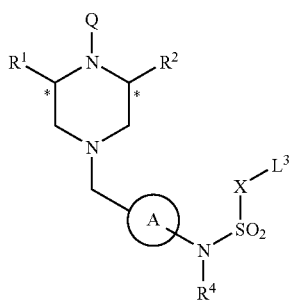

wherein $R^1$, $R^2$, $R^4$, A, X and Q are as defined above and $L^3$ represents a leaving group such as halogen with a compound of formula $R^3CH_2MgL^4$ (formula XIV) wherein $R^3$ is as defined above and $L^4$ is a suitable halogen such as chloride, in the presence of a suitable catalyst such as cobalt (II) acetylacetonate and in a suitable solvent such as tetrahydrofuran and thereafter optionally carrying out modifications according to reactions 1-3 as described above.

Compounds of formula (X) may be prepared by reaction of a compound of formula (II) with compounds of formula $L^3$—X—$SO_2$-$L^1$ (formula (XV)) where X is defined in formula (I) and $L^1$ and $L^3$ are a leaving group such as halogen, optionally in the presence of a base such as triethylamine.

Compounds of formula (VI), (VII), (VIII) and (IX) are either commercially available, described in the literature or can be prepared by analogous or similar methods.

Compounds of formula $L^3$-X—$SO_2$-$L^1$ (formula (XV)) are either commercially available, described in the literature or can be prepared by analogous or similar methods.

Pharmaceutically acceptable salts may be prepared conventionally by reaction with the appropriate acid or acid derivative.

The potencies and efficacies of the compounds of this invention for GPR38 can be determined by FLIPR assay performed on the human cloned receptor as described herein. Compounds of formula (I) have demonstrated partial or full agonist activity at the GPR38 receptor, using the FLIPR (FLuorometric Imaging Plate Reader) functional assay described herein.

Compounds of formula (I) and their pharmaceutically acceptable salts are therefore of use in the treatment of conditions or disorders which are mediated via the GPR38 receptor. In particular the compounds of formula (I) and their pharmaceutically acceptable salts are of use in the treatment of certain gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, and other disorders such as incontinence (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the GPR38 receptor. In particular the invention provides a compound of formula (I) or a pharmaceutically acceptable salt thereof for use as a therapeutic substance in the treatment of gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, and other disorders such as incontinence The invention further provides a method of treatment of conditions or disorders in mammals including humans which can be mediated via the GPR38 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the GPR38 receptor In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg or 1.0 to 200 mg, and such unit doses may be administered more than once a day, for example two or three times a day. Such therapy may extend for a number of weeks or months.

The compounds of the present invention may be used in combination preparations. For example, the compounds of the invention may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Conditions, Hardware and Software for Analytical LCMS Systems

Hardware

Agilent 1100 Gradient Pump

Agilent 1100 Autosampler

Agilent 1100 DAD Dectector

Agilent 1100 Degasser

Agilent 1100 Oven

Agilent 1100 Controller

Waters ZQ Mass Spectrometer

Sedere Sedex 55, Sedere Sedex 85 or Polymer Labs PL-ELS-2100

Software

Waters MassLynx version 4.0 SP2

Column

The column used is a Waters Atlantis, the dimensions of which are 4.6 mm×50 mm.

The stationary phase particle size is 3 μm.

Solvents

A: Aqueous solvent=Water+0.05% Formic Acid

B: Organic solvent=Acetonitrile+0.05% Formic Acid

Method

The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow Rate

The above method has a flow rate of 3 mL/min

Conditions for Open Access Mass Directed Auto Prep System (MDAP)

Hardware

Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System.

Software
MicroMass MassLynx v4.0

Column
The column used is typically a Supelco LCABZ++ column whose dimensions are 20 mm internal diameter by 100 mm in length. The stationary phase particle size is 5 μm.

Solvents
A: Aqueous solvent=Water+0.1% Formic Acid
B: Organic solvent=MeCN:Water 95:5+0.05% Formic Acid
Make up solvent=MeOH:Water 80:20+50 mmol Ammonium Acetate
Needle rinse solvent=MeOH: Water:DMSO 80:10:10

Methods
One of five methods may be used depending on the analytical retention time of the compound of interest.
All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B Flow Rate
All of the above methods have a flow rate of 20 mL/min.

Conditions Used for NMR

Hardware
Bruker 400 MHz Ultrashield
Bruker B-ACS60 Autosampler
Bruker Advance 400 Console
Bruker DPX250
Bruker AVANCE 500
Bruker DRX600

Software
User interface—NMR Kiosk
Controlling software—XWin NMR version 3.0

Chromatography
Unless stated otherwise, all chromatography was carried out using silica columns

ABBREVIATIONS

HCl—hydrochloric acid, hydrogen chloride
NaHCO$_3$—sodium hydrogen carbonate
1,2-DCE—1,2-dichloroethane,
NaOH—sodium hydroxide
DCM—dichloromethane
MeOH—methanol,
EtOAc—ethyl acetate
MgSO$_4$—magnesium sulfate
NH$_3$—ammonia
TFA—trifluoroacetic acid
Et$_2$O—diethyl ether
THF—tetrahydrofuran
CDCl$_3$—deuterochloroform
DMSO-d$_6$—dimethyl sulfoxide-d$_6$
BINAP—(±)-2,2'-bis(diphenylphosphino)-1,1'-binaphthalene
NaCl—sodium chloride
EtOH—ethanol
$^t$BuOH—tert-butanol
KOH—potassium hydroxide
Pd/C—palladium on charcoal
Na$_2$SO$_4$—sodium sulfate
DIPEA—di-isopropylethylamine, Hunig's base
K$_2$CO$_3$—potassium carbonate
1,2-DME—1,2-dimethoxyethane
MeOD—deuteromethanol
Co(acac)$_2$—cobalt (II) acetoacetonate
Boc—tert-butyloxycarbonyl
SCX—Solid-phase Cation eXchange
MDAP—Mass Directed Auto-Prep Description 1

1,1-Dimethylethyl (2S)-2-methyl-4-[(4-nitrophenyl)methyl]-1-piperazinecarboxylate (D1)

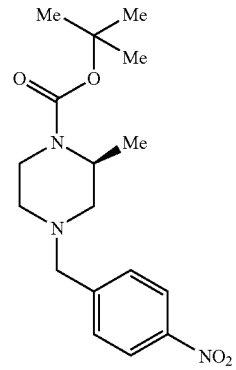

A mixture of 4-nitrobenzaldehyde (15.1 g, 0.1 mol), 1,1-dimethylethyl (2S)-2-methyl-1-piperazinecarboxylate (21.3 g, 0.09 mol), triethylamine (15 mL, 0.108 mol) and sodium tri(acetoxy)borohydride (42.4 g, 0.2 mol) in 1,2-DCE (500 mL) was stirred at room temperature overnight. Saturated aqueous NaHCO$_3$ solution (200 mL) was added and the mixture stirred for 20-30 minutes. The phases were separated and the aqueous phase was washed with DCM. The combined organics were washed with brine, dried and concentrated. Column chromatography eluting with 0-20% EtOAc/hexane gave the title compound as a yellow oil which crystallized on standing (25.61 g). δ$_H$ (CDCl$_3$, 400 MHz) 8.19 (2H, d), 7.53 (2H, d), 4.21 (1H, br.s), 3.83 (1H, d), 3.62 (1H, d), 3.50 (1H, d), 3.13 (1H, td), 2.74 (1H, m), 2.54 (1H, m), 2.20 (1H, dd), 2.08 (1H, m), 1.46 (9H, s), 1.25 (3H, d).

Alternative/larger scale preparations of D1 may be found in WO 2008/000729.

Description 2

1,1-Dimethylethyl (2S)-4-[(4-aminophenyl)methyl]-2-methyl-1-piperazinecarboxylate (D2)

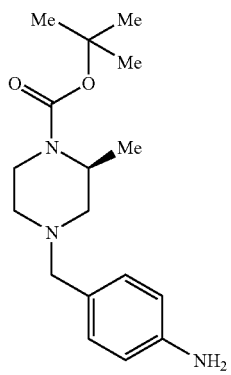

To a solution of D1 (4.62 g, 13.78 mmol) and KOH (7.79 g, 138.8 mmol) in MeOH (100 mL) was added wet (50% w/w water) 10% Pd/C (4 g) catalyst and the mixture was hydrogenated at room temperature and atmospheric pressure for 40 minutes. The catalyst was removed by filtration and the filtrate concentrated in vacuo. The residue was partitioned between DCM and water and aqueous layer further extracted with DCM (×2). The combined organics were washed with brine, dried and concentrated to give the title compound as a colourless gum (4.14 g) which was used in the next step without further purification. $\delta_H$ (CDCl$_3$, 400 MHz) 7.10 (2H, d), 6.64 (2H, d), 4.16 (1H, br.s), 3.78 (1H, m), 3.62 (2H, s), 3.42 (1H, d), 3.28 (1H, d), 3.08 (1H, td), 2.74 (1H, m), 2.58 (1H, m), 2.06 (1H, dd), 1.95 (1H, m), 1.46 (9H, s), 1.21 (3H, d).

Alternative/larger scale preparations of D2 may be found in WO 2008/000729.

Description 3

1,1-Dimethylethyl (2S)-2-methyl-4-{[4-(methylamino)phenyl]methyl}-1-piperazinecarboxylate (D3)

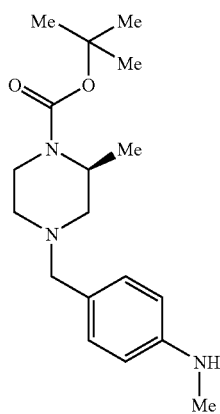

To a solution of D2 (4.14 g, 13.56 mmol) in dry MeOH (80 mL) at 50° C. under an argon atmosphere was added paraformaldehyde (1.22 g, 40.67 mmol) and sodium methoxide (3.65 g, 67.78 mmol). The mixture was stirred for ~24 h then sodium borohydride (1.54 g, 40.67 mmol) was added portionwise and the reaction stirred at 50° C. overnight. After cooling to room temperature, acetone (10 mL) was added and the solvent removed in vacuo. The residue was partitioned between DCM and water and the organic phase was washed with brine, then dried and concentrated. Column chromatography gave the title compound as a colourless, crystalline solid (3.73 g). $\delta_H$ (CDCl$_3$, 400 MHz) 7.13 (2H, d), 6.57 (2H, d), 4.16 (1H, br.s), 3.78 (1H, m), 3.67 (1H, br.s), 3.42 (1H, d), 3.30 (1H, d), 3.08 (1H, td), 2.83 (3H, s), 2.75 (1H, m), 2.59 (1H, m), 2.06 (1H, dd), 1.94 (1H, m), 1.45 (9H, s), 1.21 (3H, d).

Alternative/larger scale preparations of D3 may be found in WO 2008/000729.

Description 4

N-[4-(Hydroxymethyl)-3-methyl phenyl]acetamide (D4)

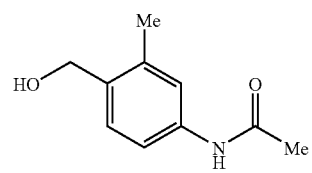

4-(Acetylamino)-2-methylbenzoic acid (2 g, 10.4 mmol) was suspended in THF (50 mL) and borane-THF complex (1M in THF, 26 mL, 26 mmol) added drop-wise over 15 minutes. The reaction mixture was stirred under argon overnight. The reaction mixture was quenched with water (51 mL) and extracted with EtOAc (×3). The combined organics were dried and concentrated. The crude product was purified by chromatography. Elution with 0-100% EtOAc/petroleum ether yielded the title compound as a cream solid (0.379 g). $\delta_H$ (MeOD, 400 MHz) 7.36 (2H, d), 7.25 (1H, d), 4.57 (2H, s), 2.31 (3H, s), 2.10 (3H, s). MS (ES$^+$): MH$^+$ 180.2.

Description 5

N-(4-Formyl-3-methylphenyl)acetamide (D5)

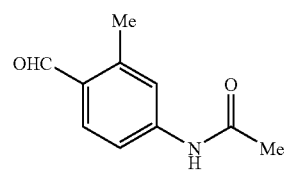

D4 (0.36 g, 2 mmol) and manganese dioxide (0.875 g, 10 mmol) were combined in acetonitrile (16 mL) and heated to 120° C. in the microwave. The solid residue was filtered off and the reaction mixture concentrated. The crude product was purified by column chromatography. Elution with 0-100% EtOAc/petroleum ether yielded the title compound as a cream solid (0.326 g). $\delta_H$ (CDCl$_3$, 400 MHz) 10.27 (1H, s), 7.79

(1H, d), 7.50 (1H, d), 7.45 (1H, s), 7.35 (1H, br.s), 2.66 (3H, s), 2.20 (3H, s). MS (ES+): MH+ 178.2.

Description 6

1,1-Dimethylethyl (2S)-4-{[4-(acetylamino)-2-methyl phenyl]methyl}-2-methyl-1-piperazinecarboxylate (D6)

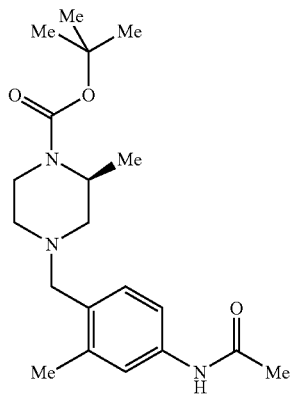

D5 (326 mg, 1.8 mmol), 1,1-dimethylethyl (2S)-2-methyl-1-piperazinecarboxylate hydrochloride (436 mg, 1.8 mmol), triethylamine (0.282 mL, 2 mmol) and sodium triacetoxyborohydride (781 mg, 3.7 mmol) were stirred together in 1,2-DCE (15 mL) for 17 h. Saturated aqueous NaHCO$_3$ was added and the reaction mixture stirred for 1 h. The organic layer was separated and washed with water and brine, then dried and concentrated. The crude product was purified by chromatography. Elution with 0-100% EtOAc/petroleum ether yielded the title compound as a colourless oil (573 mg). $\delta_H$ (CDCl$_3$, 400 MHz) 7.28 (2H, m), 7.15 (2H, m), 4.17 (1H, br.s), 3.76 (1H, d), 3.36 (2H, s), 3.00 (1H, m), 2.70 (1H, d), 2.56 (1H, d), 2.36 (3H, s), 2.17 (4H, m), 1.95 (1H, m), 1.45 (9H, s), 1.18 (3H, d). MS (ES+): MH+ 362.3.

Description 7

1,1-Dimethylethyl (2S)-4-[(4-amino-2-methylphenyl)methyl]-2-methyl-1-piperazinecarboxylate (D7)

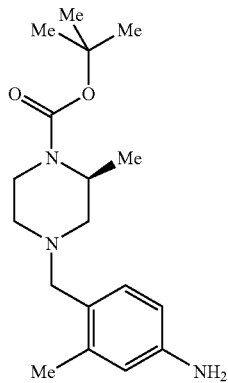

D6 (497 mg, 1.4 mmol) and KOH (1M aq soln., 5 mL) were combined in MeOH (5 mL) and heated to 140° C. for 1 h in a microwave reactor. The reaction mixture was diluted with MeOH (5 mL) and heated for 4 h 55 minutes at 130° C. in the microwave. The reaction mixture was concentrated to remove the MeOH and partitioned between DCM and water. The organic layer was dried and concentrated. The crude product was purified by chromatography. Elution with 0-100% Et$_2$O/petroleum ether followed by a column flush with 10% (2M NH$_3$ in MeOH) in DCM yielded the title compound as a yellow oil (233 mg). $\delta_H$ (CDCl$_3$, 250 MHz) 6.96 (1H, d), 6.52 (1H, d), 6.46 (1H, dd), 4.17 (1H, br.s), 3.76 (1H, m), 3.57 (2H, br.s), 3.29 (2H, AB), 3.01 (1H, td), 2.70 (1H, m), 2.56 (1H, m), 2.29 (3H, s), 2.10 (1H, dd), 1.90 (1H, td), 1.45 (9H, s), 1.18 (3H, d). MS (ES+): MNa+ 342.3, no molecular ion (MH+) observed.

Description 8

1,1-Dimethylethyl (2S)-2-methyl-4-{[2-methyl-4-(methylamino)phenyl]methyl}-1-piperazinecarboxylate (D8)

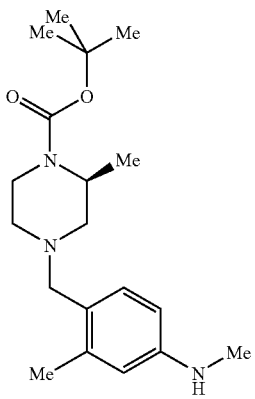

The title compound was prepared from D7 using a method similar to that described for D3.

Description 9

(3R,5S)-1-[(4-Nitrophenyl)methyl]-3,5-dimethylpiperazine (D9)

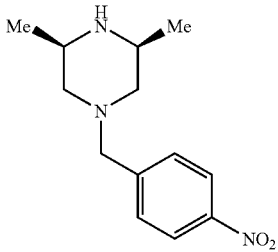

A mixture of 4-nitrobenzaldehyde (6.612 g, 43.8 mmol) and (2R,6S)-2,6-dimethylpiperazine (5 g, 43.8 mmol) in 1,2-DCE (100 mL) was stirred at room temperature for 2 h. Sodium tri(acetoxy)borohydride (13.92 g, 65.7 mmol) was added and the reaction was stirred at room temperature overweekend. The reaction mixture was diluted with DCM and washed with saturated aqueous NaHCO$_3$ solution. The aqueous wash was extracted with 10% MeOH/DCM and the combined organics were dried and concentrated. Column chromatography eluting with 0-10% MeOH/DCM gave the title compound as a cream solid (4.278 g). $\delta_H$ (CDCl$_3$, 400 MHz) 8.18 (2H, d), 7.51 (2H, d), 3.57 (2H, s), 2.97 (2H, m), 2.72 (2H, m), 1.72 (2H, m), 1.06 (6H, d). MS (ES$^+$): MH$^+$ 250.2.

Description 10

1,1-Dimethylethyl (2R,6S)-2,6-dimethyl-4-[(4-nitrophenyl)methyl]-1-piperazinecarboxylate (D10)

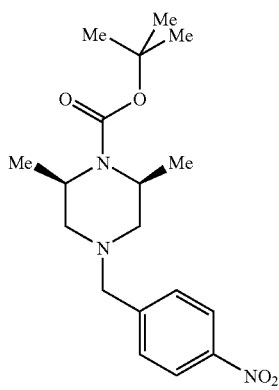

D9 (4.278 g, 17.17 mmol) was dissolved in 1,4-dioxane (180 mL) and Boc anhydride (7.494 g, 34.34 mmol) and sat. NaHCO$_3$ solution (60 mL) were added. The mixture was stirred at room temperature overnight; the mixture was filtered and the filter cake washed with DCM. The filtrate was concentrated under vacuum and the residue partitioned between DCM and water. The DCM layer was separated and the aqueous was extracted with DCM (×2). The DCM layers were combined and dried to produce a yellow oil (9.614 g). The mixture was purified by passing through an SCX cartridge to produce a yellow oil (4.787 g) which was a mixture of the title compound and unreacted D9. This whole was dissolved in DCM (60 mL) and triethylamine (2.936 mL) added followed by Boc anhydride (4.612 g, 21.13 mmol) and the mixture stirred at room temperature overnight under argon. PS-Trisamine® (6 g) was added and the mixture allowed to stir for 30 min, the polymer was filtered off and the solvent removed to produce a yellow oil (6.5621 g). Purification by column chromatography (Horizon 40+M, 0-50% Et$_2$O/petroleum ether) gave a pale yellow solid (5.245 g). This solid was dissolved in MeOH and passed down an SCX cartridge (70 g) which was eluted with MeOH followed by 2M NH$_3$ in MeOH. The solvent was removed from the ammoniacal fraction to produce a yellow solid (3.833 g) which was further purified by column chromatography (Horizon 40+M, using 0-50% Et$_2$O/petroleum ether) to give the title compound as a whitish cream solid (2.624 g). $\delta_H$ (CDCl$_3$, 400 MHz) 8.20 (2H, d), 7.57 (2H, d), 4.10 (2H, m), 3.58 (2H, s), 2.58 (2H, d), 2.21 (2H, dd), 1.47 (9H, s), 1.31 (6H, d). MS (ES$^+$): 294.3, 250.3, no molecular ion (MH$^+$) observed.

Description 11

1,1-Dimethylethyl (2R,6S)-2,6-dimethyl-4-[(4-nitrophenyl)methyl]-1-piperazinecarboxylate Alternative Procedure (D11)

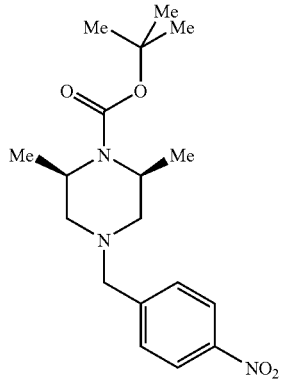

The title compound may be prepared from 4-nitrobenzaldehyde and 1,1-dimethylethyl (2R,6S)-2,6-dimethyl-1-piperazinecarboxylate using a method similar to that described for D1

Description 12

1,1-Dimethylethyl (2R,6S)-4-[(4-aminophenyl)methyl]-2,6-dimethyl-1-piperazinecarboxylate (D12)

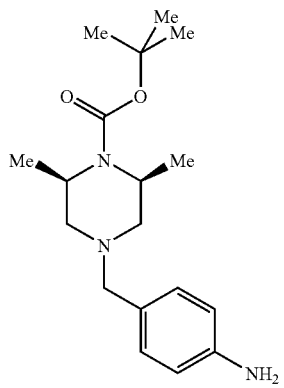

To a solution of D10 (2.62 g, 7.53 mmol) in MeOH (25 mL) and water (25 mL), heated to 80° C., was added iron powder (1.26 g, 22.54 mmol) and ammonium chloride (2.01 g, 37.58 mmol). The reaction was stirred vigorously at 80° C. for 1.5 h and then the iron residues removed by filtration through Celite®. The filtrate was concentrated and the residue partitioned between DCM and water. The aqueous layer was further extracted with DCM (×2) and the combined organics were dried and concentrated to give the crude product as a yellow foam (2.01 g). Column chromatography eluting with 0-100% Et$_2$O/petroleum ether gave the title compound (1.694 g). $\delta_H$(CDCl$_3$, 400 MHz) 7.12 (2H, d), 6.64 (2H, d), 4.05 (2H, m), 3.64 (2H, br.s), 3.36 (2H, s), 2.59 (2H, d), 2.06 (2H, dd), 1.46 (9H, s), 1.27 (6H, d). MS (ES$^+$): MH$^+$ 320.

Description 13

1,1-Dimethylethyl (2S)-4-({4-[[(6-chloro-3-pyridinyl)sulfonyl](methyl)amino]phenyl}methyl)-2-methyl-1-piperazinecarboxylate (D13)

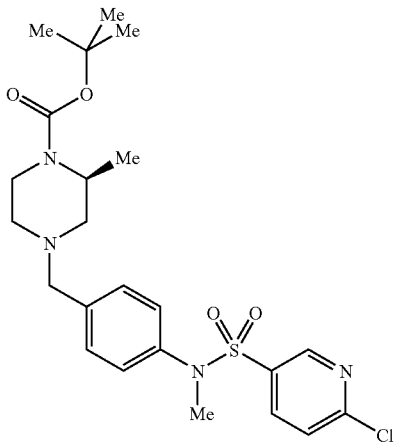

D3 (500 mg, 1.57 mmol) and 2-chloro-pyridine-5-sulfonyl chloride (330 mg, 1.57 mmol) were combined in DCM (10 mL) under Ar. Triethylamine (0.44 mL, 3.13 mmol) was added and the solution stirred overnight. The solution was diluted with DCM and washed with water. The water layer was re-extracted with DCM. The combined organic layers were washed with brine, dried and concentrated. The crude product was purified by column chromatography. Elution with 0-50% Et$_2$O/petroleum ether yielded the product as a white foam (685 mg), $\delta_H$ (CDCl$_3$, 400 MHz): 1.24 (3H, d), 1.46 (9H, s), 2.01 (1H, m), 2.16 (1H, m), 2.56 (1H, d), 2.73 (1H, d), 3.10 (1H, m), 3.22 (3H, s), 3.40-3.50 (2H, AB), 3.81 (1H, d), 4.20 (1H, br.s), 7.05 (2H, d), 7.31 (2H, d), 7.42 (1H, d), 7.74 (1H, dd), 8.54 (1H, d). MS (ES$^+$): MH$^+$ 495.1/497.1

Description 14

1,1-Dimethylethyl (2S)-4-({4-[{[6-(4-fluorophenyl)-3-pyridinyl]sulfonyl}(methyl)amino]phenyl}methyl)-2-methyl-1-piperazinecarboxylate (D14)

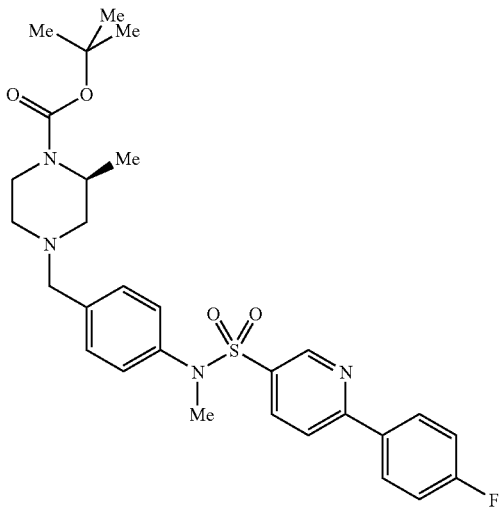

D13 (100 mg, 0.2 mmol), 4-fluorobenzene boronic acid (34 mg, 0.24 mmol), triphenylphosphine (5 mg, 0.02 mmol), palladium acetate (1 mg, 0.005 mmol) and 2M K$_2$CO$_3$ solution (0.28 mL, 0.56 mmol) were combined in 1,2-DME and heated to 150° C. in the microwave for 10 minutes. The mixture was partitioned between EtOAc and water. The aqueous layer was re-extracted with EtOAc and the combined organic layers were washed with water, dried and concentrated. The crude product was purified by column chromatography. Elution with 0-100% Et$_2$O/petroleum ether yielded the product as a yellow oil (103.1 mg), $\delta_H$ (CDCl$_3$, 400 MHz): 1.23 (3H, d), 1.46 (9H, s), 2.01 (1H, m), 2.16 (1H, m), 2.57 (1H, d), 2.74 (1H, d), 3.10 (1H, m), 3.24 (3H, s), 3.40-3.50 (2H, AB), 3.81 (1H, d), 4.20 (1H, br.s), 7.08 (2H, d), 7.20 (2H, t), 7.30 (2H, d), 7.76 (1H, dd), 7.85 (1H, dd), 8.06 (2H, m), 8.80 (1H, m). MS (ES$^+$): MH$^+$ 555.3

Description 15

1,1-Dimethylethyl (2S)-4-[(4-{[(6-chloro-3-pyridinyl)sulfonyl]amino}phenyl)methyl]-2-methyl-1-piperazinecarboxylate (D15)

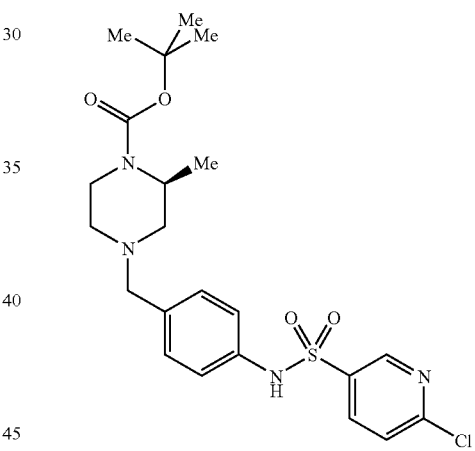

D2 (500 mg, 1.64 mmol) and pyridine (1.5 mL) were combined in DCM (5 mL). 2-chloro-pyridine-5-sulfonylchloride (314 mg, 1.48 mmol) in DCM (5 mL) was added dropwise. The solution was stirred over the weekend and the solvent removed. The residue was partitioned between DCM (25 mL) and water (25 mL). The aqueous layer was re-extracted with DCM (25 mL) and the combined organic layers washed with brine (50 mL), dried and concentrated. The crude product was purified by column chromatography. Eluting with 0-50% EtOAc/petroleum ether yielded the product as a yellow foam (470.1 mg), $\delta_H$(CDCl$_3$, 400 MHz) 1.18 (3H, d), 1.46 (9H, s), 1.97 (1H, m), 2.08 (1H, m), 2.48 (1H, d), 2.68 (1H, d), 3.07 (1H, m), 3.32-3.46 (2H, AB), 3.78 (1H, d), 4.16 (1H, br.s), 7.07 (2H, d), 7.23 (2H, d), 7.39 (1H, d), 7.96 (1H, dd), 8.72 (1H, m). MS (ES$^+$): MH$^+$ 481.2/483.1

Description 16

1,1-Dimethylethyl (2S)-4-{[4-({[6-(4-fluorophenyl)-3-pyridinyl]sulfonyl}amino)phenyl]methyl}-2-methyl-1-piperazinecarboxylate (D16)

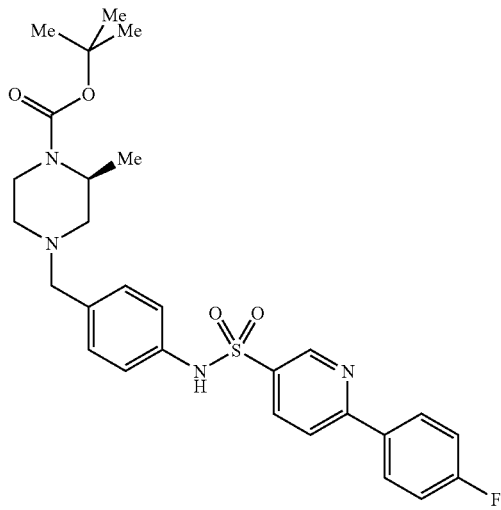

D15 (58 mg, 0.12 mmol), 4-fluorobenzene boronic acid (20 mg, 0.14 mmol), triphenylphosphine (3 mg, 0.012 mmol), 2M $K_2CO_3$ solution (0.17 mL, 0.33 mmol) and palladium acetate (0.7 mg, 0.003 mmol) were combined in 1,2-DCE (0.5 mL) and heated to 150° C. in the microwave for 10 minutes. The mixture was partitioned between EtOAc and water. The aqueous layer was re-extracted with EtOAc and the combined organic layers were washed with water, dried and concentrated. The crude product was purified by column chromatography. Elution with 0-50% EtOAc/petroleum ether yielded the product as a yellow oil (35 mg), $\delta_H$ (CDCl$_3$ 400 MHz) 1.18 (3H, d), 1.45 (9H, s), 1.70 (1H, br.s), 1.97 (1H, td), 2.08 (1H, dd), 2.49 (1H, d), 2.68 (1H, d), 3.06 (1H, m), 3.32-3.44 (2H, AB), 3.78 (1H, d), 4.15 (1H, br.s), 7.08 (2H, d), 7.17 (2H, t), 7.23 (2H, d), 7.73 (1H, d), 7.99-8.07 (3H, m), 8.98 (1H, m) MS (ES$^+$): MH$^+$ 541.2

Description 17

1,1-Dimethylethyl (2S)-2-methyl-4-{[4-({[6-(1-piperidinyl)-3-pyridinyl]sulfonyl}amino)phenyl]methyl}-1-piperazinecarboxylate (D17)

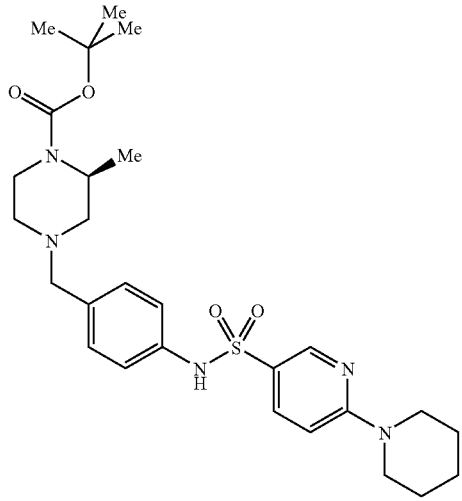

D15 (200 mg, 0.42 mmol), piperidine (141 mg, 1.66 mmol) and DIPEA (58 mg, 0.45 mmol) were combined in THF and DMF (0.75 mL each) and heated to 100° C. for 20 min in the microwave. The solvent was removed and the residues partioned between DCM and water (10 mL each). The aqueous layer was re-extracted with DCM (10 mL), and the combined organic layers washed with water (25 mL), dried and concentrated. The crude product was purified by chromatography. Elution with 0-50% EtOAc/petroleum ether yielded the product as a yellow foam (174 mg), $\delta_H$ (CDCl$_3$, 400 MHz) 1.19 (3H, d), 1.45 (9H, s), 1.57-1.61 (4H, m), 1.65-1.69 (2H, m), 1.96 (1H, m), 2.07 (1H, dd), 2.51 (1H, d), 2.70 (1H, d), 3.07 (1H, m), 3.30-3.43 (2H, AB), 3.61 (4H, m), 3.78 (1H, d), 4.15 (1H, br.s), 6.51 (1H, d), 7.08 (2H, d), 7.20 (2H, d), 7.41 (1H, br.s), 7.69 (1H, dd), 8.47 (1H, m). MS (ES$^+$): MH$^+$ 530.4

Description 18

1,1-Dimethylethyl (2S)-2-methyl-4-{[4-({[6-(4-morpholinyl)-3-pyridinyl]sulfonyl}amino)phenyl]methyl}-1-piperazinecarboxylate (D18)

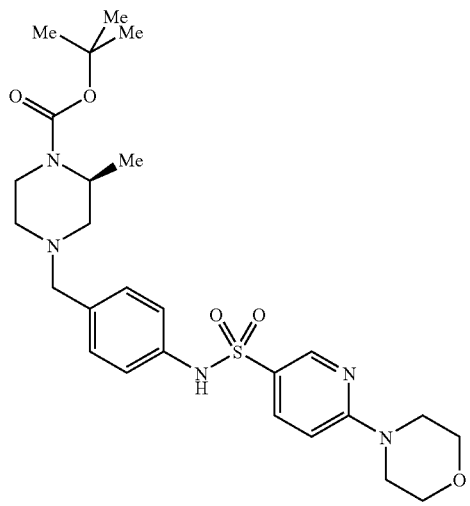

The title compound was prepared from D15 and morpholine using a method similar to that described for D17. MS (ES$^+$): MH$^+$ 532.4

Description 19

1,1-Dimethylethyl (2S)-4-({4-[[(4'-fluoro-4-biphenylyl)sulfonyl](methyl)amino]phenyl}methyl)-2-methyl-1-piperazinecarboxylate (D19)

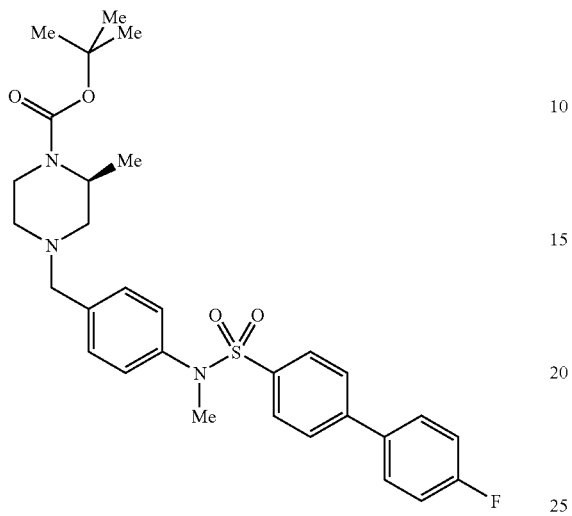

D3 (100 mg, 0.31 mmol) and triethylamine (65 ul, 0.47 mmol) were combined in dry DCM (3 mL) under argon. 4'-Fluoro-4-biphenylsulfonyl chloride (93 mg, 0.34 mmol) was added dropwise in a solution of dry DCM (3 mL). The reaction mixture was stirred at room temperature under argon for 19 h and diluted with DCM (20 mL) and washed with water then the organic layer was dried ($Na_2SO_4$) and concentrated in vacuo. The crude material was purified by chromatography eluting with 0-100% $Et_2O$/petroleum ether to afford the title compound (53 mg), $\delta_H$ ($CDCl_3$), 400 MHz: 1.23 (3H, d), 1.46 (9H, s), 2.01 (1H, m), 2.14, 1H, dd), 2.57 (1H, m), 2.74 (1H, m), 3.10 (1H, m), 3.21 (3H, s), 3.39-3.51 (2H, AB), 3.81 (1H, d), 4.19 (1H, br.s), 7.08 (2H, d), 7.17 (2H, t), 7.28 (2H, m), 7.57 (2H, dd), 7.61 (4H, s). MS ($ES^+$): $MH^+$ 554.3

Description 20

1,1-Dimethylethyl (2S)-4-[(4-{[(4'-fluoro-4-biphenyl)sulfonyl]amino}phenyl)methyl]-2-methyl-1-piperazinecarboxylate (D20)

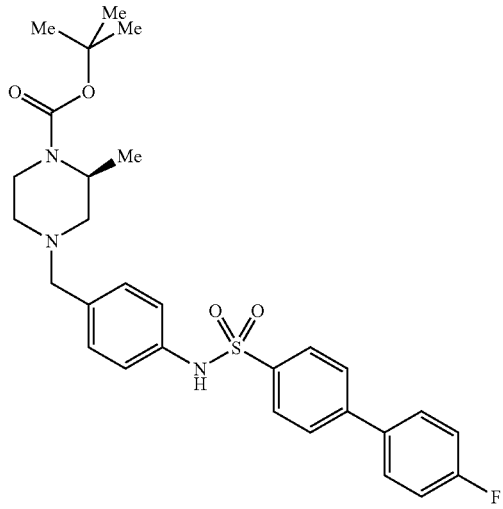

D2 (200 mg, 0.66 mmol) and triethylamine (137 ul, 0.98 mmol) were combined in dry DCM (5 mL) under argon. A solution of 4'-fluoro-4-biphenylsulfonyl chloride (213 mg, 0.79 mmol) in dry DCM (5 mL) was added dropwise. The reaction mixture was stirred at room temperature under argon for 22 h and diluted with DCM (20 mL) and washed with water. The organic layer was dried ($Na_2SO_4$) and concentrated in vacuo. The crude material was purified by chromatography eluting with 0-100% $Et_2O$/petroleum ether to afford the title compound (234 mg). MS ($ES^+$): $MH^+$ 540.2

Description 21

1,1-Dimethylethyl (2R,6S)-4-[(4-{[(6-chloro-3-pyridinyl)sulfonyl]amino}phenyl)methyl]-2,6-dimethyl-1-piperazinecarboxylate (D21)

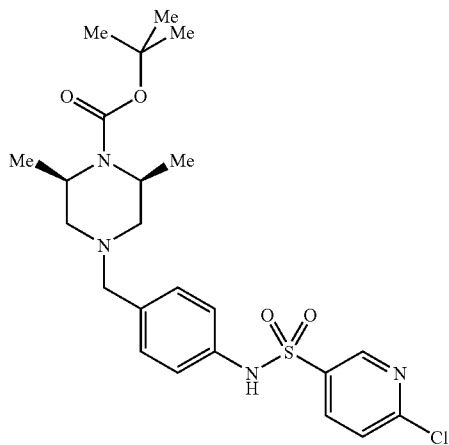

D12 (200 mg, 0.63 mmol) was dissolved in DCM (2 mL) and pyridine (0.61 mL, 7.5 mmol) was added dropwise. The reaction mixture was cooled to 0° C. in an ice-bath and 6-chloro-3-pyridinesulfonyl chloride (120 mg, 0.56 mmol) was added dropwise in a solution of DCM (2 mL). Reaction mixture stirred under argon and gradually allowed to warm to room temperature. After 18 h the mixture was partitioned between DCM and water. The organic layer dried ($Na_2SO_4$) and concentrated in vacuo. The crude residue was purified by chromatography eluting with 0-100% EtOAc/petroleum ether to afford the title compound (295 mg). MS ($ES^+$): $MH^+$ 495.3/497.3.

Description 22

1,1-Dimethylethyl (2R,6S)-4-{[4-({[6-(4-fluorophenyl)-3-pyridinyl]sulfonyl}amino)phenyl]methyl}-2,6-dimethyl-1-piperazinecarboxylate (D22)

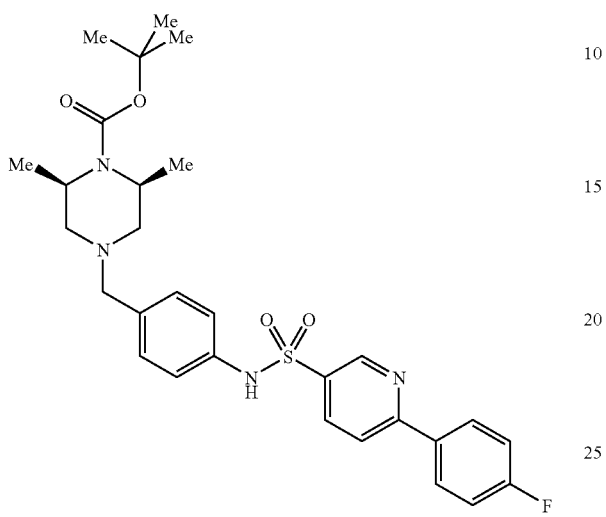

D21 (100 mg, 0.2 mmol), (4-fluorophenyl)boronic acid (34 mg, 0.24 mmol), sodium carbonate (86 mg, 0.81 mmol) and tetrakis(triphenylphosphine)palladium(0) (12 mg, 0.01 mmol) were suspended in dry 1,2-DME (2 mL) and deionised water (2 mL) and heated to 140° C. in the microwave for 10 minutes. The crude reaction mixture was partitioned between DCM and water. The aqueous layer was extracted with DCM and the organic layer was dried (Na$_2$SO$_4$) and concentrated in vacuo. The crude material was purified by chromatography eluting with 0-100% EtOAc/petroleum ether to afford the title compound (97 mg). MS (ES$^+$): MH$^+$ 555.3

Description 23

1,1-Dimethylethyl (2S)-4-[(4-{[[(6-chloro-3-pyridinyl)sulfonyl]amino}-2-methyl phenyl)methyl]-2-methyl-1-piperazinecarboxylate (D23)

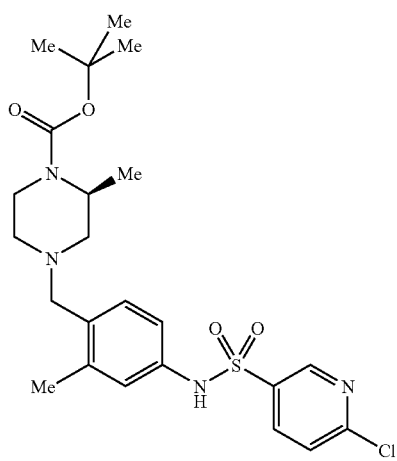

D7 (100 mg, 0.31 mmol) in dry DCM (1.05 mL) and pyridine (0.30 mL, 3.8 mmol) was stirred to 0° C. under argon and 6-chloro-3-pyridinesulfonyl chloride (60 mg, 0.28 mmol) in dry DCM (1.05 mL) added dropwise. The reaction mixture was stirred under argon and allowed to warm to room temperature. After 17 h, the reaction mixture was diluted with water/DCM. The aqueous layer was extracted with DCM, the organic layer dried (Na$_2$SO$_4$) and solvent removed under vacuum. The product was purified by column chromatography (Biotage Horizon 40+S) eluting with petroleum ether/Et$_2$O to afford the title compound as a colourless oil (148 mg). MS (ES$^+$): MH$^+$ 495.1/497.1.

Description 24

1,1-Dimethylethyl (2S)-4-{[4-({[6-(4-fluorophenyl)-3-pyridinyl]sulfonyl}amino)-2-methylphenyl]methyl}-2-methyl-1-piperazinecarboxylate (D24)

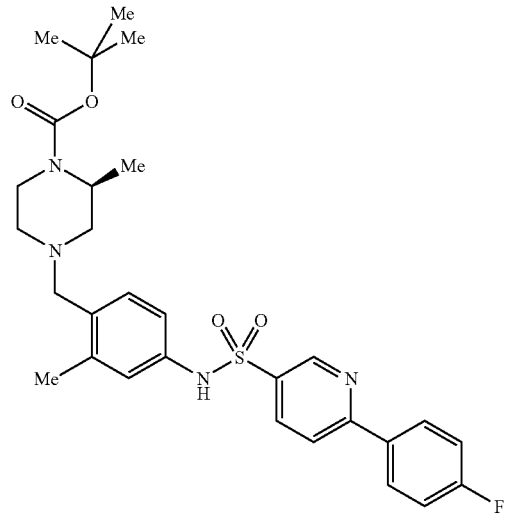

D23 (148 mg, 0.3 mmol), (4-fluorophenyl)boronic acid (50 mg, 0.36 mmol), sodium carbonate (127 mg, 1.2 mmol) and tetrakis(triphenylphosphine)palladium(0) (17 mg, 0.015 mmol) were suspended in 1,2-DME (2 mL) and deionised water (2 mL) and heated to 140° C. in the microwave for 10 minutes. The reaction mixture was partitioned between DCM and water. The aqueous layer was extracted with DCM and the organic layer was dried (Na$_2$SO$_4$) and concentrated in vacuo. The crude material was purified by chromatography on silica eluting with 0-100% EtOAc/petroleum ether to afford the title compound (122 mg). MS (ES$^+$): MH$^+$ 555.3

Description 25

1,1-Dimethylethyl (2S)-4-({4-[[(6-chloro-3-pyridinyl)sulfonyl](methyl)amino]-2-methylphenyl}methyl)-2-methyl-1-piperazinecarboxylate (D25)

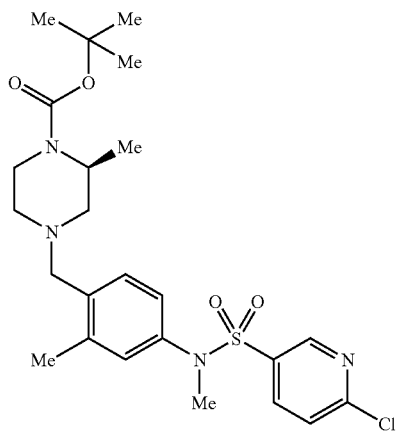

The title compound was prepared from D8 and 2-chloropyridine-5-sulfonyl chloride using a method similar to that described for D15 except that the reaction time was overnight. The work-up involved concentration of the reaction mixture and purification by elution through an SCX cartridge (MeOH then 0.2M NH$_3$ in MeOH), followed by column chromatography eluting with 0-20% EtOAc/petroleum ether. $\delta_H$ (CDCl$_3$, 400 MHz) 8.55 (1H, dd), 7.76 (1H, dd), 7.42 (1H, d), 7.21 (1H, d), 6.96 (1H, d), 6.80 (1H, dd), 6.86 (1H, dd), 4.20 (1H, br.s), 3.79 (1H, m), 3.38 (2H, AB), 3.20 (3H, s), 3.05 (1H, m), 2.69 (1H, m), 2.56 (1H, m), 2.32 (3H, s), 2.19 (1H, m), 1.99 (1H, m), 1.46 (9H, s), 1.21 (3H, d). MS (ES$^+$): MH$^+$ 509/511.

Description 26

1,1-Dimethylethyl (2S)-4-({4-[({6-[(4-fluorophenyl)amino]-3-pyridinyl}sulfonyl) (methyl)amino]-2-methyl phenyl}methyl)-2-methyl-1-piperazinecarboxylate (D26)

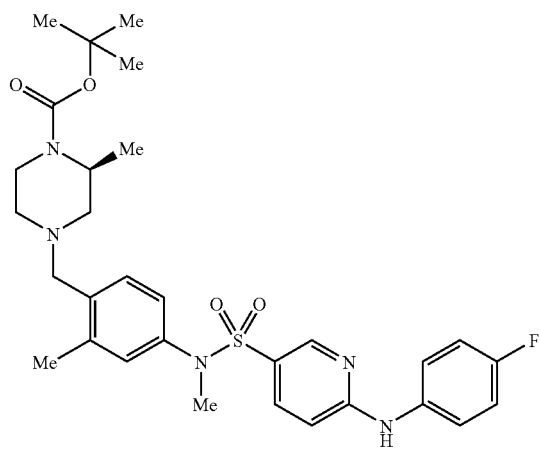

A mixture of BINAP (7.1 mg, 0.0114 mmol), palladium (II) acetate (1.5 mg, 0.007 mmol) and cesium carbonate (56 mg, 0.171 mmol) in 1,4-dioxane (2 mL) was sonicated for 1 h. The resulting solution was treated with 4-fluoroaniline (14 mg, 0.125 mmol) and D25 (58 mg, 0.114 mmol) dissolved in 1,4-dioxane (2 mL). The reaction was stirred at 75° C. for 1.5 h then further 4-fluoroaniline (14 mg) was added and heating and stirring were continued for a further 1.5 h. After standing overnight at room temperature another portion each of palladium (II) acetate and BINAP were added and the reaction heated at 75° C. overnight. The reaction mixture was cooled, concentrated and partitioned between EtOAc and water (5 mL each). The organic phase was dried, concentrated and purified by MDAP to give impure title compound as a cream solid (7 mg). This was purified by column chromatography eluting with 1-30% EtOAc/petroleum ether to give the title compound as a clear oil (2.7 mg). $\delta_H$ (CDCl$_3$, 400 MHz) 8.37 (1H, d), 7.51 (1H, dd), 7.34 (2H, dd), 7.19 (1H, d), 7.09 (2H, m), 7.02 (1H, m), 6.86 (1H, dd), 6.83 (1H, br.s), 6.61 (1H, d), 4.19 (1H, br.s), 3.79 (1H, m), 3.37 (2H, AB), 3.17 (3H, s), 3.05 (1H, m), 2.69 (1H, m), 2.56 (1H, m), 2.33 (3H, s), 2.18 (1H, m), 1.97 (1H, m), 1.46 (9H, s), 1.20 (3H, d). MS (ES$^+$): MH$^+$ 584.3.

Description 27

1,1-Dimethylethyl (2S)-4-[(4-{[(5-bromo-3-pyridinyl)sulfonyl]amino}-2-methyl phenyl)methyl]-2-methyl-1-piperazinecarboxylate (D27)

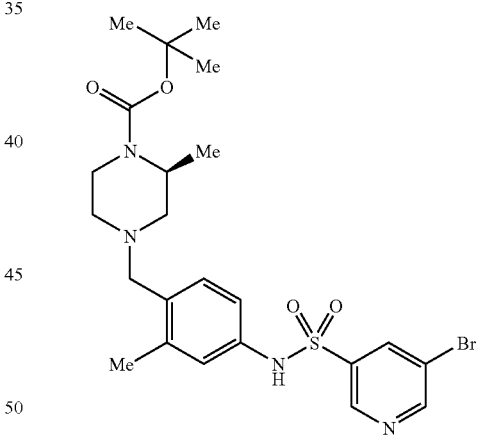

The title compound was prepared from D7 and 3-bromopyridine-5-sulfonyl chloride using a method similar to that described for D15 except that the reaction time was overnight and column chromatography was carried out eluting with 0-100% Et$_2$O/petroleum ether. $\delta_H$ (CDCl$_3$, 400 MHz) 8.83 (1H, d), 8.80 (1H, d), 8.12 (1H, t), 7.16 (1H, d), 7.13 (1H, br.s), 6.92 (1H, d), 6.86 (1H, dd), 4.17 (1H, br.s), 3.77 (1H, d), 3.34 (2H, s), 2.99 (1H, m), 2.64 (1H, m), 2.51 (1H, d), 2.31 (3H, s), 2.14 (1H, m), 1.96 (1H, m), 1.46 (9H, s), 1.17 (3H, d). MS (ES$^+$): MH$^+$ 539/541.

Description 28

1,1-Dimethylethyl (2S)-4-{[4-({[5-(4-fluorophenyl)-3-pyridinyl]sulfonyl}amino)-2-methylphenyl]methyl}-2-methyl-1-piperazinecarboxylate (D28)

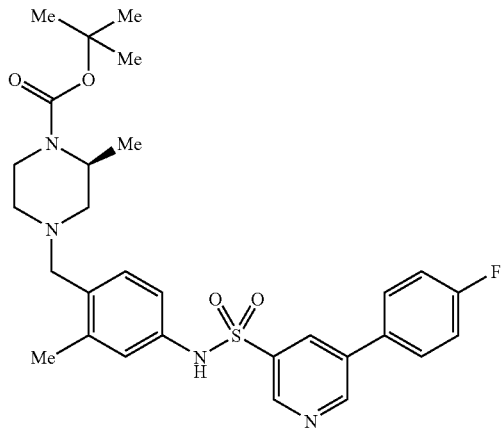

The title compound was prepared from D27 using a method similar to that described for D22 except that column chromatography was carried out eluting with 0-100% Et$_2$O/petroleum ether. δ$_H$ (CDCl$_3$, 400 MHz) 8.92 (2H, dd), 8.12 (1H, t), 7.47 (2H, m), 7.15-7.21 (3H, m), 6.92 (1H, d), 6.88 (1H, dd), 6.60 (1H, s), 4.15 (1H, br.s), 3.76 (1H, m), 3.33 (2H, s), 3.00 (1H, m), 2.63 (1H, m), 2.49 (1H, m), 2.30 (3H, s), 2.13 (1H, dd), 1.94 (1H, td), 1.45 (9H, s), 1.15 (3H, d). MS (ES$^+$): MH$^+$ 555.3.

Description 29

1,1-Dimethylethyl (2S)-4-({4-[({6-[(4-fluorophenyl)methyl]-3-pyridinyl}sulfonyl)amino]phenyl}methyl)-2-methyl-1-piperazinecarboxylate (D29)

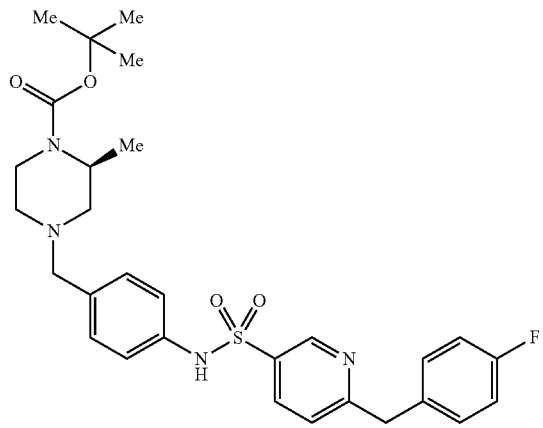

To Co(acac)$_2$ (16 mg, 0.0624 mmol) in THF (1.5 mL) under argon and cooled to 0° C. was added a solution of 4-fluorobenzylmagnesium chloride in THF (4.16 mL, 0.25M, 1.04 mmol) and the mixture stirred at room temperature for 10 minutes. A solution of D15 (100 mg, 0.208 mmol) in THF (1.5 mL) was added dropwise and the reaction was stirred at room temperature overnight. Further 4-fluorobenzylmagnesium chloride solution (4.16 mL) and Co(acac)$_2$ (16 mg) in THF (1 mL) was added dropwise and the reaction mixture was stirred at room temperature for 3.5 h. The solvent was removed in vacuo and the residue was partitioned between EtOAc and water. The organic layer was dried and concentrated to give the crude product as a yellow solid. Purification by column chromatography eluting with an EtOAc/petroleum ether gradient gave the title compound as a yellow oil (76 mg). δ$_H$ (CDCl$_3$, 400 MHz) 8.86 (1H, dd), 7.89 (1H, dd), 7.22 (2H, d), 7.13-7.19 (3H, m), 6.97-7.03 (4H, m), 6.86 (1H, br.s), 4.17 (1H, m), 4.15 (2H, s), 3.78 (1H, m), 3.38 (2H, AB), 3.07 (1H, m), 2.68 (1H, m), 2.50 (1H, m), 2.09 (1H, dd), 1.97 (1H, td), 1.45 (9H, s), 1.19 (3H, d). MS (ES$^+$): MH$^+$ 555.2.

Description 30

4-Nitro-2-(trifluoromethyl)benzaldehyde (D30)

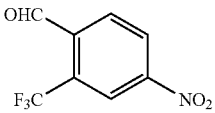

To 4-nitro-2-(trifluoromethyl)benzonitrile (100 mg, 0.463 mmol) in toluene (3 mL) at 0° C. under argon was added DIBAL-H (0.51 mL, 1M in toluene, 0.51 mmol) and the reaction stirred for 3.75 h. MeOH and sulphuric acid were added and the reaction mixture was warmed to room temperature and stirred for 1 h. The mixture was concentrated and the residue was portioned between EtOAc (10 mL) and water (10 mL). The organic phase was dried and concentrated to give the crude product which was purified by column chromatography eluting with 0-15% EtOAc/petroleum ether to give the title compound as a yellow oil (91 mg), δ$_H$ (CDCl$_3$, 400 MHz) 10.47 (1H, s), 8.66 (1H, d), 8.56 (1H, dd), 8.33 (1H, d).

Description 31

1,1-Dimethylethyl (2S)-2-methyl-4-{[4-nitro-2-(trifluoromethyl)phenyl]methyl}-1-piperazinecarboxylate (D31)

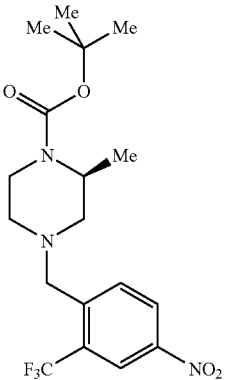

A mixture of D30 (88 mg, 0.402 mmol), 1,1-dimethylethyl (2S)-2-methyl-1-piperazinecarboxylate (95 mg, 0.402 mmol) and sodium tri(acetoxy)borohydride (128 mg, 0.603 mmol) in 1,2-DCE (3 mL) was stirred at room temperature over-weekend.

Further sodium tri(acetoxy)borohydride (43 mg, 0.201 mmol) was added and the reaction stirred for 3.5 h and was then quenched by addition of NaHCO$_3$ solution (5 mL). The mixture was extracted with DCM (3×10 mL) and the combined organics were dried and concentrated in vacuo to give the crude product. Purification by column chromatography eluting with 0-20% EtOAc/petroleum ether gave the title compound as a yellow oil (95 mg). δ$_H$ (CDCl$_3$, 400 MHz) 8.52 (1H, d), 8.40 (1H, dd), 8.12 (1H, d), 4.24 (1H, br.s), 3.86

(1H, m), 3.71 (2H, s), 3.14 (1H, m), 2.72 (1H, m), 2.54 (1H, m), 2.32 (1H, m), 2.17 (1H, m), 1.47 (9H, s), 1.28 (3H, d). MS (ES+): MH+ 404.1.

Description 32

1,1-Dimethylethyl (2S)-4-{[4-amino-2-(trifluoromethyl)phenyl]methyl}-2-methyl-1-piperazinecarboxylate (D32)

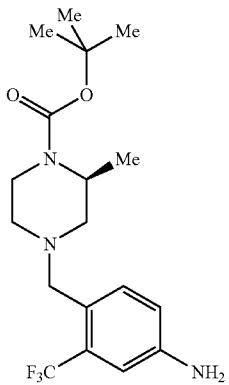

A mixture of D31 (93 mg, 0.23 mmol), triethylamine (0.32 mL, 2.31 mmol) and 5% platinum on carbon (20 mg) in MeOH (3 mL) was stirred under an atmosphere of hydrogen at room temperature for 2 h. The catalyst was removed by filtration through Celite and the filtrate concentrated to give the crude product. Purification by column chromatography eluting with 0-20% EtOAc/petroleum ether gave the title compound as a yellow oil (80 mg). $\delta_H$ (CDCl$_3$, 400 MHz) 7.49 (1H, d), 6.92 (1H, d), 6.80 (1H, dd), 4.19 (1H, br.s), 3.78-3.81 (3H, m), 3.47 (2H, s), 3.07 (1H, m), 2.71 (1H, d), 2.56 (1H, m), 2.16 (1H, dd), 2.02 (1H, m), 1.46 (9H, s), 1.22 (3H, d). MS (ES+): MH+ 374.2.

Description 33

1,1-Dimethylethyl (2S)-4-{[4-{[(6-chloro-3-pyridinyl)sulfonyl]amino}-2-(trifluoromethyl)phenyl]methyl}-2-methyl-1-piperazinecarboxylate (D33)

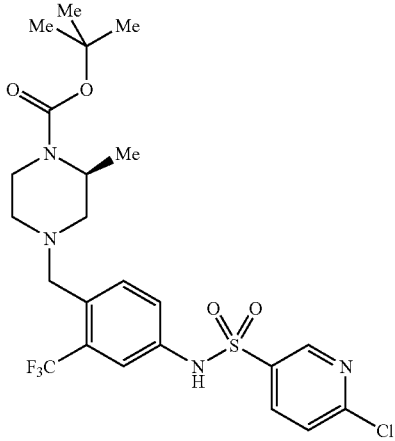

To a solution of D32 (78 mg, 0.21 mmol) and pyridine (25 uL, 0.32 mmol) in DCM (2 mL) was added a solution of 2-chloro-pyridine-5-sulfonylchloride (49 mg, 0.23 mmol) in DCM (1 mL). The reaction was stirred for 3 h and further 2-chloro-pyridine-5-sulfonylchloride (9 mg) was added. After stirring for 1.5 h further 2-chloro-pyridine-5-sulfonylchloride (9 mg) was added. After stirring for 1.5 h further pyridine (8 uL) and DCM (1 mL) were added and the reaction was stirred overnight. The mixture was partitioned between DCM (5 mL) and water (5 mL). The aqueous layer was re-extracted with DCM (10 mL) and the combined organic layers were dried and concentrated. The crude product was semi-purified by elution through an SCX cartridge (MeOH then 2M NH$_3$ in MeOH). The ammoniacal fraction was then purified twice by column chromatography eluting with 0-20% EtOAc/petroleum ether for the first column and then 0-50% EtOAc/petroleum ether for the second to give the title compound (60 mg). $\delta_H$ (CDCl$_3$, 400 MHz) 8.76 (1H, dd), 7.99 (1H, dd), 7.82 (1H, br.s), 7.72 (1H, d), 7.43 (1H, dd), 7.37 (1H, d), 7.33 (1H, dd), 4.17 (1H, br.s), 3.79 (1H, m), 3.53 (2H, s), 3.07 (1H, m), 2.66 (1H, m), 2.49 (1H, d), 2.21 (1H, dd), 2.06 (1H, m), 1.46 (9H, s), 1.21 (3H, d). MS (ES+): MH+ 549/551.

Description 34

1,1-Dimethylethyl (2S)-4-{[4-({[6-(4-fluorophenyl)-3-pyridinyl]sulfonyl}amino)-2-(trifluoromethyl)phenyl]methyl}-2-methyl-1-piperazinecarboxylate (D34)

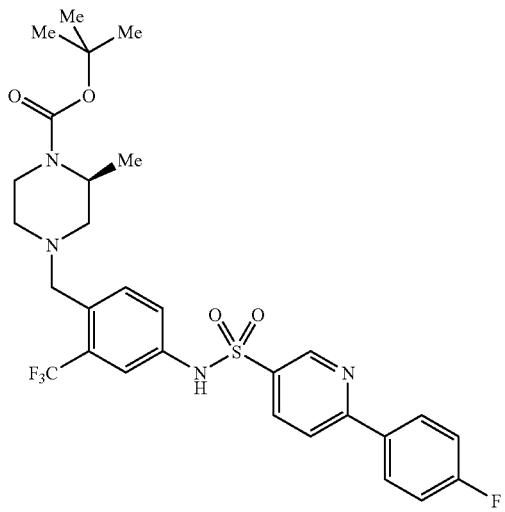

D33 (27 mg, 0.049 mmol), (4-fluorophenyl)boronic acid (10.3 mg, 0.074 mmol), sodium carbonate (21 mg, 0.196 mmol) and bis(triphenylphosphine)palladium (II) chloride (1.7 mg, 0.002 mmol) were mixed in 1,2-DME (0.5 mL) and water (0.28 mL) and heated to 120° C. in the microwave for 20 minutes. The crude reaction mixture was partitioned between DCM (5 mL) and water (5 mL). The aqueous layer was extracted with DCM (2×5 mL) and the combined organics were dried (MgSO$_4$) and concentrated in vacuo to give the crude product. The reaction was repeated starting with D32 (37 mg) and the two crude products were combined to give 75 mg of material which was purified by column chromatography eluting with 0-100% EtOAc/petroleum ether to afford the title compound (54 mg). $\delta_H$ (CDCl$_3$, 400 MHz) 9.02 (1H, dd), 8.10 (1H, dd), 8.02 (2H, m), 7.77 (1H, dd), 7.72 (1H, d), 7.51 (1H, br.s), 7.38 (1H, d), 7.34 (1H, dd), 7.18 (2H, m), 4.18 (1H, br.s), 3.79 (1H, m), 3.52 (2H, s), 3.07 (1H, m), 2.66 (1H, m), 2.49 (1H, m), 2.20 (1H, dd), 2.05 (1H, td), 1.46 (9H, s), 1.20 (3H, d). MS (ES+): MH+ 609.3.

Description 35

1,1-Dimethylethyl (2S)-4-({4-[({6-[(4-fluorophenyl)amino]-3-pyridinyl}sulfonyl)amino]phenyl}methyl)-2-methyl-1-piperazinecarboxylate (D35)

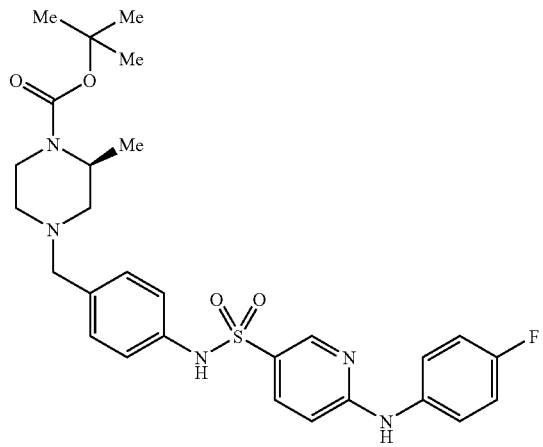

A mixture of (S)-BINAP (23.3 mg, 0.038 mmol), palladium (II) acetate (5 mg, 0.023 mmol) and cesium carbonate (180 mg, 0.563 mmol) in 1,4-dioxane (3 mL) was sonicated for 1 h. The resulting solution was treated with 4-fluoroaniline (46 mg, 0.413 mmol) and D15 (180 mg, 0.375 mmol) dissolved and the reaction was stirred at 75° C. for 1.5 h. Further 4-fluoroaniline (46 mg) was added and heating and stirring were continued for a further 1.5 h. The reaction was then cooled and after standing over-weekend at room temperature, the mixture was evaporated. The residue was dissolved in EtOAc (25 mL) and washed with water (20 mL), then dried (MgSO$_4$) and concentrated to give the crude product. Purification by column chromatography eluting with 0-50% EtOAc/hexane gave the title compound (114 mg). MS (ES$^+$): MH$^+$ 556.2.

Description 36

1,1-Dimethylethyl (2S)-4-({4-[({6-[(3-fluorophenyl)amino]-3-pyridinyl}sulfonyl)amino]phenyl}methyl)-2-methyl-1-piperazinecarboxylate (D36)

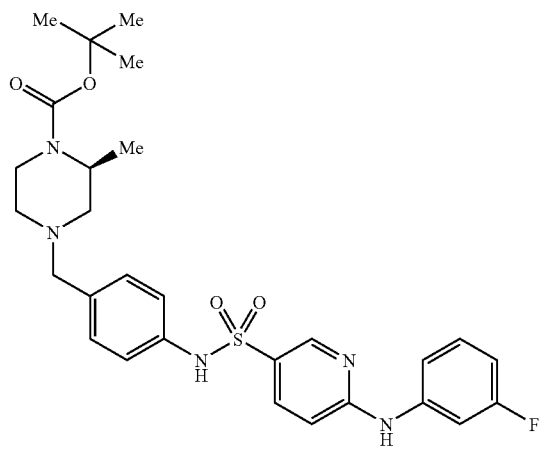

The title compound was prepared from D15 and 3-fluoroaniline using a method similar to that described for D35. MS (ES$^+$): MH$^+$ 556.2.

Description 37

1,1-Dimethylethyl (2S)-4-({4-[({6-[(4-fluorophenyl)(methyl)amino]-3-pyridinyl}sulfonyl)amino]phenyl}methyl)-2-methyl-1-piperazinecarboxylate (D37)

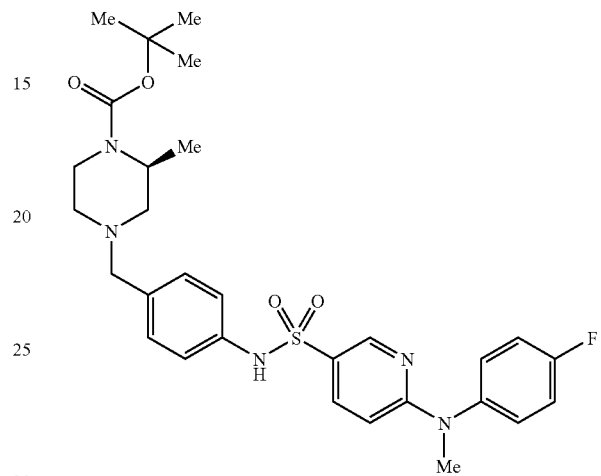

The title compound was prepared from D15 and N-methyl-4-fluoroaniline using a method similar to that described for D35. MS (ES$^+$): MH$^+$ 570.2.

Example 1

6-(4-Fluorophenyl)-N-methyl-N-(4-{[(3S)-3-methyl-1-piperazinyl]methyl}phenyl)-3-pyridinesulfonamide (E1)

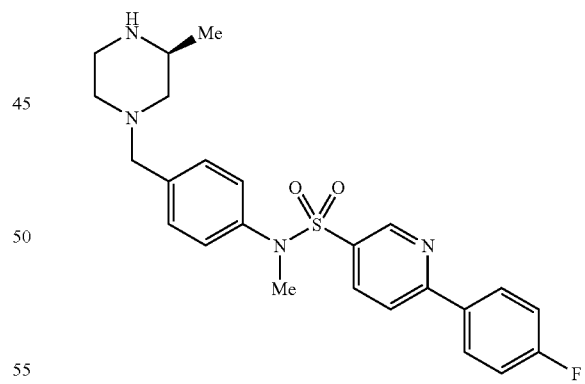

D14 (103 mg, 0.19 mmol) was taken up in DCM (4 mL) and the solution cooled in an ice-bath. TFA (1 mL) was added and the solution stirred for 2.5 h. The solvent was removed and the residue eluted through a 2 g SCX cartridge with MeOH (20 mL) then 2M NH$_3$ in MeOH (20 mL). The ammonia containing fractions were concentrated to yield the product as a clear oil (69 mg). δ$_H$(CDCl$_3$, 400 MHz) 1.05 (3H, d), 1.74 (1H, t), 2.06 (1H, td), 2.29 (1H, br.s), 2.73-2.77 (2H, m), 2.88-2.99 (3H, m), 3.24 (3H, s), 3.48 (2H, s), 7.08 (2H, d), 7.20 (2H, t), 7.29 (2H, d), 7.76 (1H, dd), 7.85 (1H, dd), 8.06 (2H, m), 8.81 (1H, m) MS (ES$^+$): MH$^+$ 455.

This whole was treated with 1.1 eq of 1M HCl/Et$_2$O to give the hydrochloride salt of the title compound (71.7 mg). MS (ES$^+$): MH$^+$ 455.2

Example 2

6-(4-Fluorophenyl)-N-(4-{[(3S)-3-methyl-1-piperazinyl]methyl}phenyl)-3-pyridinesulfonamide (E2)

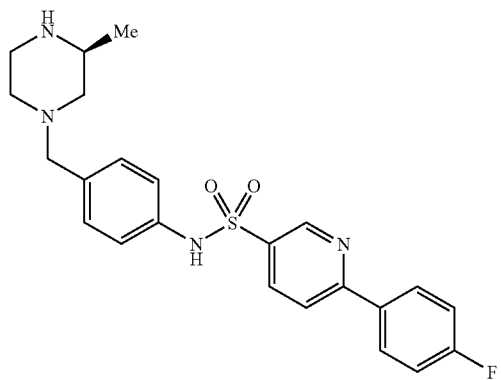

D16 (35 mg, 0.065 mmol) was taken up in DCM (4 mL). TFA (1 mL) was added with ice-bath cooling and the solution stirred for two hours. The solvent was removed. The residue was taken up in MeOH (20 mL) and applied to a 1 g SCX cartridge which was eluted with MeOH (20 mL) and 2M NH$_3$ in MeOH (20 mL). The ammonia containing fractions were concentrated. The crude product was purified by column chromatography. Elution with 0-10% 2M NH$_3$ in MeOH/DCM yielded the product as as a white solid (25.5 mg), δ$_H$ (CDCl$_3$, 400 MHz) 1.02 (3H, d), 1.67 (1H, t), 1.99 (1H, td), 2.70 (2H, d), 2.84-2.99 (3H, m), 3.41 (2H, s), 4.00 (2H, br.s), 7.06 (2H, d), 7.14-7.22 (4H, m), 7.73 (1H, d), 7.98-8.06 (3H, m), 8.98 (1H, m). MS (ES$^+$): MH$^+$ 441.2

This whole was treated with 1.1 eq of 1M HCl/Et$_2$O to give the hydrochloride salt of the title compound (28 mg). MS (ES$^+$): MH$^+$ 441.0

Example 3

N-(4-{[(3S)-3-Methyl-1-piperazinyl]methyl}phenyl)-6-(1-piperidinyl)-3-pyridinesulfonamide (E3)

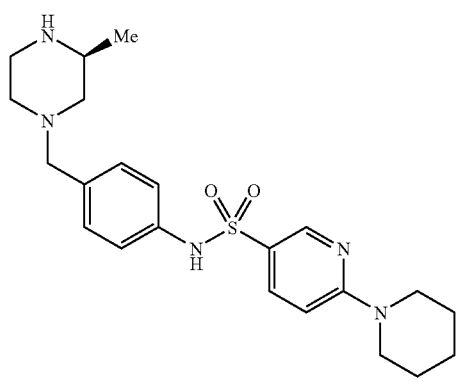

D17 (174 mg, 0.33 mmol) was taken up in DCM (8 mL) and cooled in an ice-bath. TFA (2 mL) was added and the solution stirred for 3 h. The solvent was removed. The residues were taken up in MeOH (5 mL) and applied to a 2 g SCX cartridge which was eluted with MeOH (20 mL) then 2M NH$_3$ in MeOH (20 mL). The ammonia containing fractions were concentrated to yield the product as an orange foam (141.2 mg), δ$_H$ (CDCl$_3$, 400 MHz) 1.00 (3H, d), 1.60-1.68 (8H, m), 1.96 (2H, m), 2.70 (2H, m), 2.81-2.96 (3H, m), 3.40 (2H, s), 3.62 (4H, m), 6.50 (1H, d), 7.02 (2H, d), 7.20 (2H, d), 7.64 (1H, dd), 8.47 (1H, d). MS (ES$^+$): MH$^+$ 430.2

This whole was treated with 1.1 eq of 1M HCl/Et$_2$O to give the hydrochloride salt of the title compound (152 mg). MS (ES$^+$): MH$^+$ 430.2

Example 4

N-(4-{[(3S)-3-Methyl-1-piperazinyl]methyl}phenyl)-6-(4-morpholinyl)-3-pyridinesulfonamide (E4)

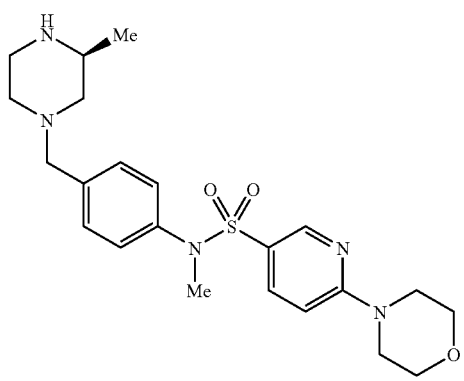

The title compound was prepared in a similar manner to E3 using 1,1-dimethylethyl (2S)-2-methyl-4-{[4-({[6-(4-morpholinyl)-3-pyridinyl]sulfonyl}amino)phenyl]methyl}-1-piperazinecarboxylate (D18). MS (ES$^+$): MH$^+$ 432.3

Example 5

4'-Fluoro-N-methyl-N-(4-{[(3S)-3-methyl-1-piperazinyl]methyl}phenyl)-4-biphenylsulfonamide (E5)

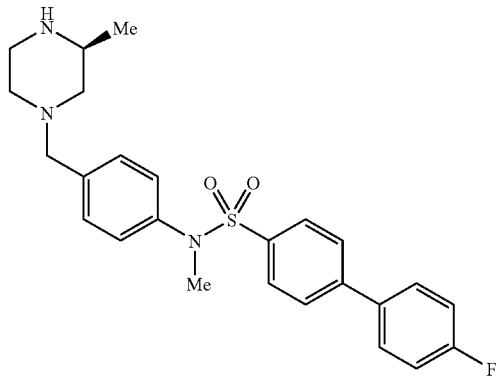

D19 (53 mg, 0.096 mmol) in DCM (10 mL) was stirred under argon at room temperature and TFA (2.5 mL) added dropwise. After 19 h the mixture was concentrated in vacuo. The residue was partitioned between DCM and water and DCM layer extracted with water. The aqueous layer was basified to pH14 (conc. NaOH) and extracted with EtOAc. The EtOAc layer was dried ($Na_2SO_4$) and concentrated in vacuo. Pure product was also seen in DCM layer therefore this was dried ($Na_2SO_4$) and concentrated in vacuo. Products from the DCM and EtOAc layers were combined to afford title compound (39 mg), $\delta_H$ (CDCl$_3$, 400 MHz) 1.24 (3H, d), 2.15 (1H, m), 2.38 (1H, m), 2.84 (2H, d), 3.05 (1H, m), 3.20 (3H, s), 3.19-3.26 (2H, m), 3.53 (2H, s), 7.10 (2H, d), 7.17 (2H, t), 7.25 (2H, d), 7.56-7.64 (6H, m). MS (ES$^+$): MH$^+$ 454.2

The whole was dissolved in MeOH (1 mL) and treated with 1M HCl/Et$_2$O (0.1 mL). Solvent was removed to afford the hydrochloride salt of the title compound (29 mg). MS (ES$^+$): MH$^+$ 454.0

Example 6

4'-Fluoro-N-(4-{[(3S)-3-methyl-1-piperazinyl]methyl}phenyl)-4-biphenylsulfonamide (E6)

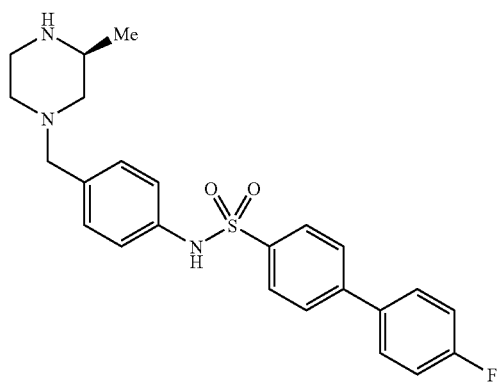

D20 (234 mg, 0.43 mmol) was dissolved in DCM (20 mL). TFA (5 mL) was added dropwise and reaction mixture stirred under argon at room temperature. After 1 h the crude reaction mixture was concentrated in vacuo. The residue was partitioned between DCM and water. The aqueous layer was basified to pH14 with conc. NaOH and extracted with EtOAc. The EtOAc layer was dried ($Na_2SO_4$) and concentrated in vacuo. The basic aqueous layer was further extracted with DCM (5×20 mL) to yield further crude product. DCM layer was dried ($Na_2SO_4$) and concentrated in vacuo. Crude materials were combined and purified by column chromatography (Biotage Horizon 25+S) eluting with 0-20% MeOH/DCM to afford the title compound (82.9 mg), $\delta_H$ (CDCl$_3$, 400 MHz) 1.07 (3H, d), 1.77 (1H, t), 2.08 (1H, m), 2.71 (2H, d), 2.88-2.95 (2H, m), 3.02 (1H, m), 3.42 (2H, s), 3.81 (2H, br.s), 7.06 (2H, d), 7.14 (2H, t), 7.19 (2H, d), 7.52 (2H, dd), 7.59 (2H, d), 7.83 (2H, d). MS (ES$^+$): MH$^+$ 440.3

The whole was dissolved in MeOH (1 mL) and treated with 1M HCl/Et$_2$O (0.23 mL). Solvent was removed to afford the hydrochloride salt of the title compound (75 mg). MS (ES$^+$): MH$^+$ 440.2

Example 7

N-(4-{[(3R,5S)-3,5-Dimethyl-1-piperazinyl]methyl}phenyl)-6-(4-fluorophenyl)-3-pyridinesulfonamide (E7)

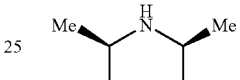

D22 (97 mg, 0.18 mmol) was dissolved in DCM (10 mL). TFA (2.5 mL) was added dropwise and reaction mixture stirred under argon at room temperature. After 1 h the crude reaction mixture was concentrated in vacuo. The residue was partitioned between DCM and water. The aqueous layer was basified to pH14 with concentrated sodium hydroxide solution (50% w/v) and extracted with DCM. The product remained in aqueous layer therefore this was adjusted to pH9 with 2M HCl and re-extracted with DCM. The DCM layer was dried ($Na_2SO_4$) and concentrated in vacuo. The crude material was purified by column chromatography eluting with 0-10% MeOH/DCM to afford the title compound (46 mg), $\delta_H$ (CDCl$_3$, 400 MHz) 1.07 (6H, d), 1.69 (1H, t), 2.70 (2H, m), 2.96 (2H, m), 3.42 (2H, s), 7.07 (2H, d), 7.15-7.23 (4H, m), 7.74 (1H, d), 7.99-8.08 (3H, m), 8.98 (1H, s). MS (ES$^+$): MH$^+$ 455.2

The whole was dissolved in MeOH (1 mL) and treated with 1M HCl/Et$_2$O (0.122 mL). Solvent was removed to afford the hydrochloride salt of the title compound (42 mg). MS (ES$^+$): MH$^+$ 455.2

Example 8

6-(4-Fluorophenyl)-N-(3-methyl-4-{[(3S)-3-methyl-1-piperazinyl]methyl}phenyl)-3-pyridinesulfonamide (E8)

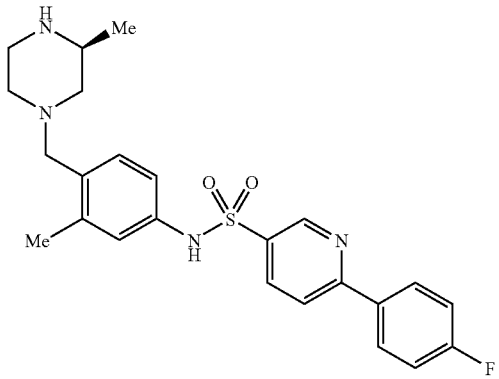

D24 (122 mg, 0.22 mmol) in dry DCM (10 mL) was stirred at room temperature under argon. TFA (2.5 mL) was added dropwise and the reaction mixture stirred at room temperature under argon. After 30 minutes the reaction mixture was concentrated under vacuum. The residue was partitioned between DCM and water and DCM layer extracted with water. The pH of the aqueous layer was adjusted to pH8-9 using 2M NaOH and extracted into DCM. The organic layer was dried (Na$_2$SO$_4$) and the solvent taken of under vacuum. The product was purified by column chromatography (Biotage Horizon 20+S) eluting with 0-10% MeOH/DCM to afford the title compound as a yellow solid (72 mg), $\delta_H$ (CDCl$_3$, 400 MHz) 1.07 (3H, d), 1.78 (1H, t), 2.08 (1H, m), 2.27 (3H, s), 2.68 (2H, m), 2.84-2.92 (2H, m), 2.99 (1H, m+H$_2$O), 3.35 (2H, s), 6.89 (1H, dd), 6.93 (1H, d), 7.16 (3H, m), 7.74 (1H, dd), 8.01 (2H, dd), 8.08 (1H, d), 8.98 (1H, m). MS (ES$^+$): MH$^+$ 455.1

The whole was dissolved in MeOH and 1M HCl/Et$_2$O (0.190 mL) added and solvent was removed to afford the hydrochloride salt of the title compound (76 mg). MS (ES$^+$): MH$^+$ 455.1

Example 9

6-[(4-Fluorophenyl)amino]-N-methyl-N-(3-methyl-4-{[(3S)-3-methyl-1-piperazinyl]methyl}phenyl)-3-pyridinesulfonamide (E9)

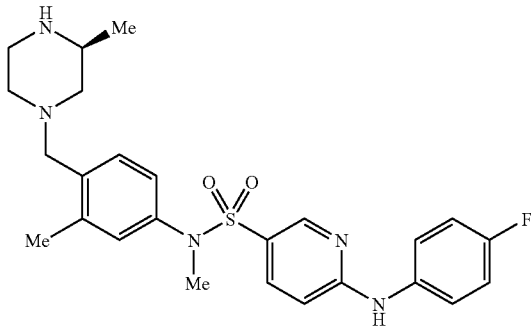

The title compound was prepared from D26 by a method similar to that used for E1 except that the reaction was carried out at room temperature for 4 h in a 2:1 mixture of DCM/TFA and 0.4M NH$_3$/MeOH was used as the second eluent for the SCX purification. $\delta_H$ (CDCl$_3$, 400 MHz) 8.38 (1H, d), 7.51 (1H, dd), 7.34 (2H, m), 7.20 (1H, d), 7.09 (2H, m), 7.01 (1H, d), 6.86 (1H, dd), 6.83 (1H, br.s), 6.61 (1H, d), 3.39 (2H, s), 3.16 (3H, s), 2.65-2.95 (3H, m), 2.72 (2H, m), 2.31 (3H, s), 2.04 (1H, m), 1.70 (1H, m), 1.03 (3H, s). MS (ES$^+$): MH$^+$ 484.3.

Example 10

5-(4-Fluorophenyl)-N-(3-methyl-4-{[(3S)-3-methyl-1-piperazinyl]methyl}phenyl)-3-pyridinesulfonamide (E10)

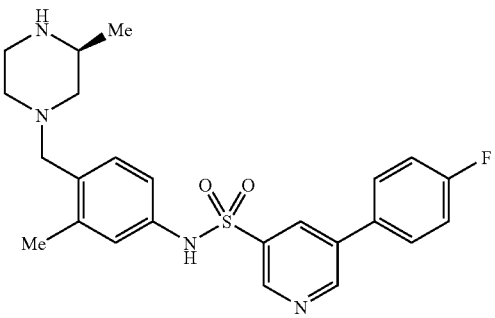

The title compound was prepared from D28 by a method similar to that used for E1 except that the reaction was carried out at room temperature for 3.5 h. $\delta_H$ (CDCl$_3$, 400 MHz) 8.92 (2H, dd), 8.11 (1H, t), 7.46 (2H, m), 7.18 (3H, m), 6.87-6.92 (2H, m), 3.35 (2H, s), 2.91 (1H, m), 2.85 (1H, m), 2.80 (1H, m), 2.66 (2H, m), 2.60 (br.s), 2.29 (3H, s), 1.99 (1H, td), 1.67 (1H, t), 0.99 (3H, d). MS (ES$^+$): MH$^+$ 455.3.

Example 11

6-[(4-Fluorophenyl)methyl]-N-(4-{[(3S)-3-methyl-1-piperazinyl]methyl}phenyl)-3-pyridinesulfonamide (E11)

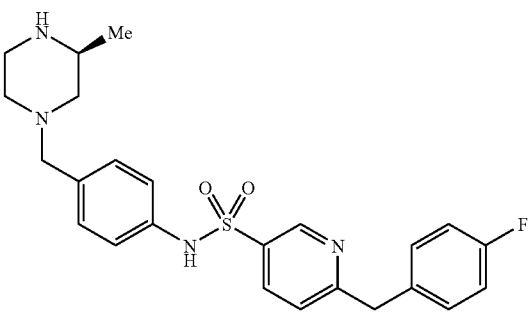

D29 (76 mg, 0.137 mmol) in DCM (10 mL) was stirred under argon at room temperature and TFA (2.5 mL) added dropwise. After 0.5 h the mixture was concentrated in vacuo. The residue was partitioned between DCM and water and the aqueous layer was basified to pH9 (dilute NaOH) then extracted with DCM. The organic extract was dried (Na$_2$SO$_4$) and concentrated in vacuo to give a white solid (17 mg). The aqueous layer was adjusted to pH8 and extracted with further DCM which was dried and combined with the first batch of solid. This mixture was concentrated to give the title compound as a white solid (41 mg). $\delta_H$ (MeOD, 400 MHz) 8.72 (1H, d), 8.01 (1H, dd), 7.34 (1H, d), 7.16-7.23 (4H, m), 6.98-7.04 (4H, m), 4.13 (2H, s), 3.42 (2H, s), 2.92 (1H, m), 2.79-2.87 (3H, m), 2.72 (2H, m), 2.02 (1H, m), 1.72 (1H, t), 1.29 (1H, br.s), 1.03 (3H, d). MS (ES+): MH+ 455.1.

This whole was dissolved in MeOH, 1M HCl/Et$_2$O (108 uL) added and solvent was removed to afford the hydrochloride salt of the title compound (46 mg). MS (ES+): MH+ 455.2.

Example 12

6-(4-Fluorophenyl)-N-[4-{[(3S)-3-methyl-1-piperazinyl]methyl}-3-(trifluoromethyl)phenyl]-3-pyridinesulfonamide (E12)

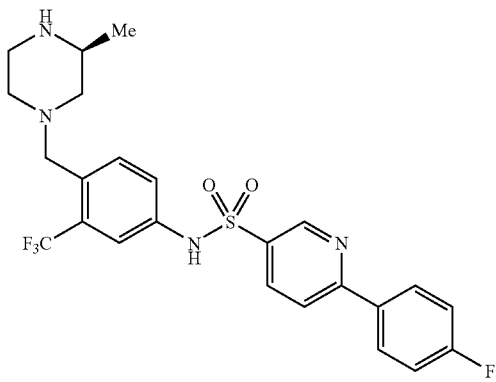

D34 (54 mg, 0.089 mmol) in DCM (1 mL) was stirred at room temperature and TFA (0.25 mL) added. After 1.25 h the mixture was diluted with DCM (5 mL) and water (5 mL) then basified to pH15 (10% aq. NaOH solution). The aqueous was extracted with DCM (2×5 mL) then adjusted to pH9. This solution was then extracted with DCM (3×5 mL) and the combined organics were dried and concentrated to give 10 mg material. All organic and aqueous extracts were combined and taken up in MeOH and filtered. The filtrate was partially concentrated and applied to an SCX cartridge. Due to blockage of the cartridge, the silica was removed and stirred with MeOH. The MeOH was decanted off and the silica was then stirred with 2M NH$_3$ in MeOH. The silica was removed by filtration and the filtrate was concentrated to a yellow oily solid. This was purified by column chromatography eluting with 0-20% (2M NH$_3$ in MeOH)/DCM to give the title compound as a white solid (11 mg). δ$_H$ (MeOD, 400 MHz) 8.92 (1H, d), 8.19 (1H, dd), 8.07 (2H, m), 7.95 (1H, d), 7.58 (1H, d), 7.42 (1H, d), 7.32 (1H, dd), 7.21 (2H, m), 3.59 (2H, s), 3.14 (2H, m), 3.00 (1H, m), 2.80 (2H, m), 2.24 (1H, m), 2.00 (1H, m), 1.28 (1H, br.s), 1.16 (3H, d). MS (ES+): MH+ 509.0.

This whole was dissolved in MeOH, 1M HCl/Et$_2$O (22 uL) added and solvent was removed to afford the hydrochloride salt of the title compound (11.8 mg).

Example 13

6-[(4-Fluorophenyl)amino]-N-(4-{[(3S)-3-methyl-1-piperazinyl]methyl}phenyl)-3-pyridinesulfonamide (E13)

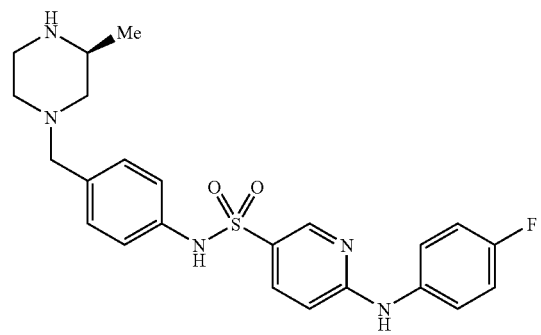

D35 (114 mg, 0.205 mmol) was dissolved in 1,4-dioxane (5 mL) and treated with 4M HCl/1,4-dioxane (2 mL) at room temperature for 1.5 h. Further 4M HCl/1,4-dioxane (2 mL) was added and the reaction stirred for a further 1 h. The reaction was evaporated to dryness and the resulting solid was triturated with acetone (3×5 mL), then dissolved in MeOH and evaporated to give the dihydrochloride salt of the title compound as a pale green solid (115 mg). MS (ES+): MH+ 456.2.

Example 14

6-[(3-Fluorophenyl)amino]-N-(4-{[(3S)-3-methyl-1-piperazinyl]methyl}phenyl)-3-pyridinesulfonamide (E14)

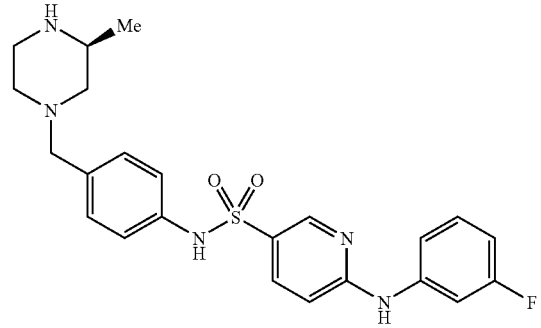

The dihydrochloride salt of the title compound was prepared from D36 using a similar method to that described for E13. MS (ES+): MH+ 456.2.

Example 15

6-[(4-Fluorophenyl)(methyl)amino]-N-(4-{[(3S)-3-methyl-1-piperazinyl]methyl}phenyl)-3-pyridine-sulfonamide (E15)

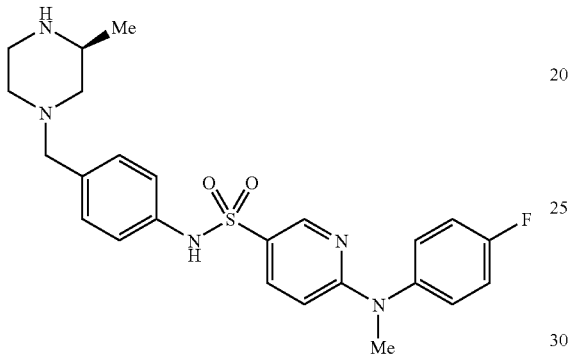

The dihydrochloride salt of the title compound was prepared from D37 using a similar method to that described for E13. MS (ES+): MH+ 470.2.

GPR38 FLIPR Functional Agonist Assay Protocol 24 hours prior to assay, CHO-K1 cells stably expressing the GPR38 receptor were seeded (10,000 cells/well) into poly-D-lysine coated 384-well black-wall, clear-bottom microtitre plates (Greiner). On the day of assay, media was aspirated from cell plates using a cell washer (leaving 10 ul of media). Cells were immediately loaded with loading buffer [Tyrodes (Elga water+145 mM NaCl+5 mM KCl+20 mM HEPES+10 mM glucose+1 mM $MgCl_2$)+1.5 mM $CaCl_2$+ 0.714 mg/mL Probenicid (predissolved in 1 M NaOH)+0.25 mM brilliant black+2 uM Fluo 4 dye], and incubated at 37.5° C. for 1 hour.

Plates were then assayed on a FLuorometric Imaging Plate Reader (FLIPR, Molecular Devices).

Master compound plates were prepared in 100% DMSO. A top concentration of 3 mM was used (giving 12 μM final concentration in assay) and this was serially diluted 1 in 4. 1 ul from the master plate was transferred to a daughter plate, to which 50 μl of compound dilution buffer (Tyrodes+1 mg/mL BSA+1.5 mM $CaCl_2$) was added. In the FLIPR, 10 ul of test compound was added to the cells and changes in fluorescence measured over a 1 minute timeframe. Maximum change in fluorescence over baseline was used to determine agonist response and concentration response curves were constructed, using a 4-parameter logistic equation.

Exemplified compounds of the invention have a pEC50>6 in the FLIPR assay,

The invention claimed is:
1. A compound of formula (I):

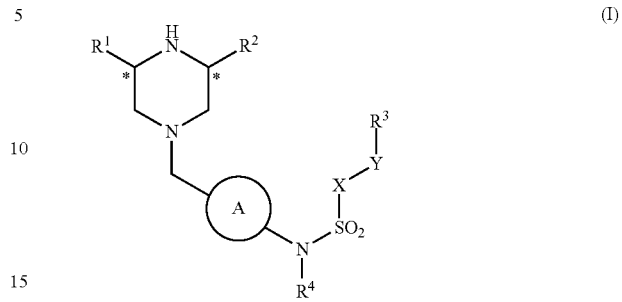

wherein:
A is phenyl optionally substituted with up to three substituents independently selected from halogen, $C_{(1-4)}$alkyl, $CF_3$ and $C_{(1-4)}$alkoxy;
$R^1$ is hydrogen or methyl;
$R^2$ is hydrogen or methyl;
$R^3$ is optionally substituted phenyl, morpholinyl or piperidinyl;
X is optionally substituted phenyl or pyridyl;
$R^4$ is hydrogen or methyl; and
Y is a bond, NH, $NCH_3$ or $CH_2$;
wherein when $R^3$ is a substituted phenyl, morpholinyl or piperidinyl or X is a substituted phenyl or pyridyl, each of said substituted phenyl, morpholinyl, piperidinyl or pyridyl is independently substituted by 1, 2 or 3 substituents, each independently selected from halogen, $C_{(1-4)}$ alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^5$, $NR^5R^6$, $NHCOR^5$, $NHSO_2R^5$, $C(O)CF_3$, $C(O)C_{(1-4)}$alkyl, $C(O)C_{(3-7)}$cycloalkyl, $C(O)OC_{(1-4)}$alkyl, $C(O)OC_{((3-7)}$cycloalkyl, $OC(O)C_{(1-4)}$alkyl, $OC(O)C_{(3-7)}$cycloalkyl, $CONH_2$, $CONHR^5$, $CONR^5R^6$, $SOR^6$, $SO_2CF_3$, $SO_2R^6$, $OSO_2R^6$, $OSO_2CF_3$, $SO_2NH_2$, $SO_2NHR^5$, and $SO_2NR^5R^6$, wherein $R^5$ and $R^6$ may be the same or different and represent $C_{(1-4)}$alkyl;
or a pharmaceutically acceptable salt thereof.
2. The compound or salt according to claim 1, wherein the (piperazinyl)methylene substituent and X are para- to each other across ring A.
3. The compound or salt according to claim 2, wherein $R^3$ is phenyl optionally substituted by halo.
4. The compound or salt according to claim 2, wherein $R^3$ is unsubstituted morpholinyl.
5. The compound or salt according to claim 2, wherein $R^3$ is unsubstituted piperidinyl.
6. The compound or salt according to claim 2, wherein X is unsubstituted phenyl or unsubstituted pyridyl.
7. A compound selected from:
6-(4-Fluorophenyl)-N-methyl-N-(4-{[(3S)-3-methyl-1-piperazinyl]methyl}phenyl)-3-pyridinesulfonamide;
6-(4-Fluorophenyl)-N-(4-{[(3S)-3-methyl-1-piperazinyl]methyl}phenyl)-3-pyridinesulfonamide;
N-(4-{[(3S)-3-Methyl-1-piperazinyl]methyl}phenyl)-6-(1-piperidinyl)-3-pyridinesulfonamide;
N-(4-{[(3S)-3-methyl-1-piperazinyl]methyl}phenyl)-6-(4-morpholinyl)-3-pyridinesulfonamide;
4'-Fluoro-N-methyl-N-(4-{[(3S)-3-methyl-1-piperazinyl]methyl}phenyl)-4-biphenylsulfonamide;
4'-Fluoro-N-(4-{[(3S)-3-methyl-1-piperazinyl]methyl}phenyl)-4-biphenylsulfonamide;

N-(4-{[(3R,5S)-3,5-Dimethyl-1-piperazinyl]methyl}phenyl)-6-(4-fluorophenyl)-3-pyridinesulfonamide;

6-(4-Fluorophenyl)-N-(3-methyl-4-{[(3S)-3-methyl-1-piperazinyl]methyl}phenyl)-3-pyridinesulfonamide;

6-[(4-Fluorophenyl)amino]-N-methyl-N-(3-methyl-4-{[(3S)-3-methyl-1-piperazinyl]methyl}phenyl)-3-pyridinesulfonamide;

5-(4-Fluorophenyl)-N-(3-methyl-4-{[(3S)-3-methyl-1-piperazinyl]methyl}phenyl)-3-pyridinesulfonamide;

6-[(4-Fluorophenyl)methyl]-N-(4-{[(3S)-3-methyl-1-piperazinyl]methyl}phenyl)-3-pyridinesulfonamide;

6-(4-Fluorophenyl)-N-[4-{[(3S)-3-methyl-1-piperazinyl]methyl}-3-(trifluoromethyl)phenyl]-3-pyridinesulfonamide;

6-[(4-Fluorophenyl)amino]-N-(4-{[(3S)-3-methyl-1-piperazinyl]methyl}phenyl)-3-pyridinesulfonamide;

6-[(3-Fluorophenyl)amino]-N-(4-{[(3S)-3-methyl-1-piperazinyl]methyl}phenyl)-3-pyridinesulfonamide; and 6-[(4-Fluorophenyl)(methyl)amino]-N-(4-{[(3S)-3-methyl-1-piperazinyl]methyl}phenyl)-3-pyridinesulfonamide;

or a pharmaceutically acceptable salt thereof.

8. A pharmaceutical composition comprising the compound or salt according to claim 1 and a pharmaceutically acceptable carrier.

9. A pharmaceutical composition comprising the compound or salt according to claim 7 and a pharmaceutically acceptable carrier.

* * * * *